United States Patent
Benschop et al.

(10) Patent No.: US 10,577,415 B2
(45) Date of Patent: Mar. 3, 2020

(54) ANTI-CGRP/ANTI-IL-23 BISPECIFIC ANTIBODIES AND USES THEREOF

(71) Applicant: Eli Lilly and Company, Indianapolis, IN (US)

(72) Inventors: Robert Jan Benschop, Indianapolis, IN (US); Stephen John Demarest, San Diego, CA (US); Xiufeng Wu, San Diego, CA (US)

(73) Assignee: Eli Lilly and Company, Indianapolis, IN (US)

( * ) Notice: Subject to any disclaimer, the term of this patent is extended or adjusted under 35 U.S.C. 154(b) by 7 days.

(21) Appl. No.: 15/963,167

(22) Filed: Apr. 26, 2018

(65) Prior Publication Data

US 2018/0319880 A1 Nov. 8, 2018

Related U.S. Application Data

(60) Provisional application No. 62/500,754, filed on May 3, 2017.

(51) Int. Cl.
| | |
|---|---|
| *A61K 39/395* | (2006.01) |
| *C07K 16/24* | (2006.01) |
| *C07K 16/18* | (2006.01) |
| *A61K 39/00* | (2006.01) |

(52) U.S. Cl.
CPC .......... *C07K 16/244* (2013.01); *A61K 39/395* (2013.01); *A61K 39/39591* (2013.01); *C07K 16/18* (2013.01); *A61K 2039/505* (2013.01); *C07K 2317/31* (2013.01); *C07K 2317/522* (2013.01); *C07K 2317/524* (2013.01); *C07K 2317/526* (2013.01); *C07K 2317/53* (2013.01); *C07K 2317/565* (2013.01); *C07K 2317/567* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | |
|---|---|---|
| 9,023,358 B2 | 5/2015 | Beidler et al. |
| 9,073,991 B2 | 7/2015 | Allan et al. |
| 2011/0305711 A1 | 12/2011 | Allan et al. |

OTHER PUBLICATIONS

Mikami et al. Calcitonin gene-related peptide enhances experimental autoimmune encephalomyelitis by promoting Th17-cell functions. Int Immunol. Nov. 2012; 24(11):681-91.*
Schou et al. Calcitonin gene-related peptide and pain: a systematic review. J Headache Pain. Dec. 2017;18(1):34. Epub Mar. 16, 2017.*
Mabry R, et al Protein Engineering Design and Selection, vol. 23, No. 3, pp. 115-127, 2010.
Kabat et al., Ann. NY Acad. Sci., vol. 190, pp. 382-393, 1971.
Klein et al., mAbs, vol. 4, No. 6, pp. 1-11, 2012.
Carter et al., J. Immunol. Methods, vol. 248, pp. 7-15, 2001.
Gunasekaran, et al., J. Biol. Chem., vol. 285, pp. 19637-19646, 2010.
Zhu et al., Protein Science, vol. 6, pp. 781-788, 1997.
Igawa et al., Protein Eng. Des. Sel., vol. 23 pp. 667-677, 2010.
*Methods in Enzymology* 182: 83-89 (1990).

* cited by examiner

*Primary Examiner* — Dong Jiang
(74) *Attorney, Agent, or Firm* — Robert L. Sharp

(57) ABSTRACT

IgG bispecific antibodies are provided that bind human Calcitonin Gene Related Peptide (CGRP) and human Interleukin-23 (IL-23) and are characterized as having high affinity and strong simultaneous neutralizing properties to both human CGRP and human IL-23. The bispecific antibodies of the invention are useful for treating various autoimmune diseases including Inflammatory Bowel Disease, such as Crohn's Disease (CD) and Ulcerative Colitis (UC), and other autoimmune diseases such as psoriatic Arthritis (PsA), ankylosing spondylitis (AS) and atopic dermatitis (AtD). The bispecific antibodies of the invention are useful for treating pain associated with the aforementioned diseases.

15 Claims, 1 Drawing Sheet

Specification includes a Sequence Listing.

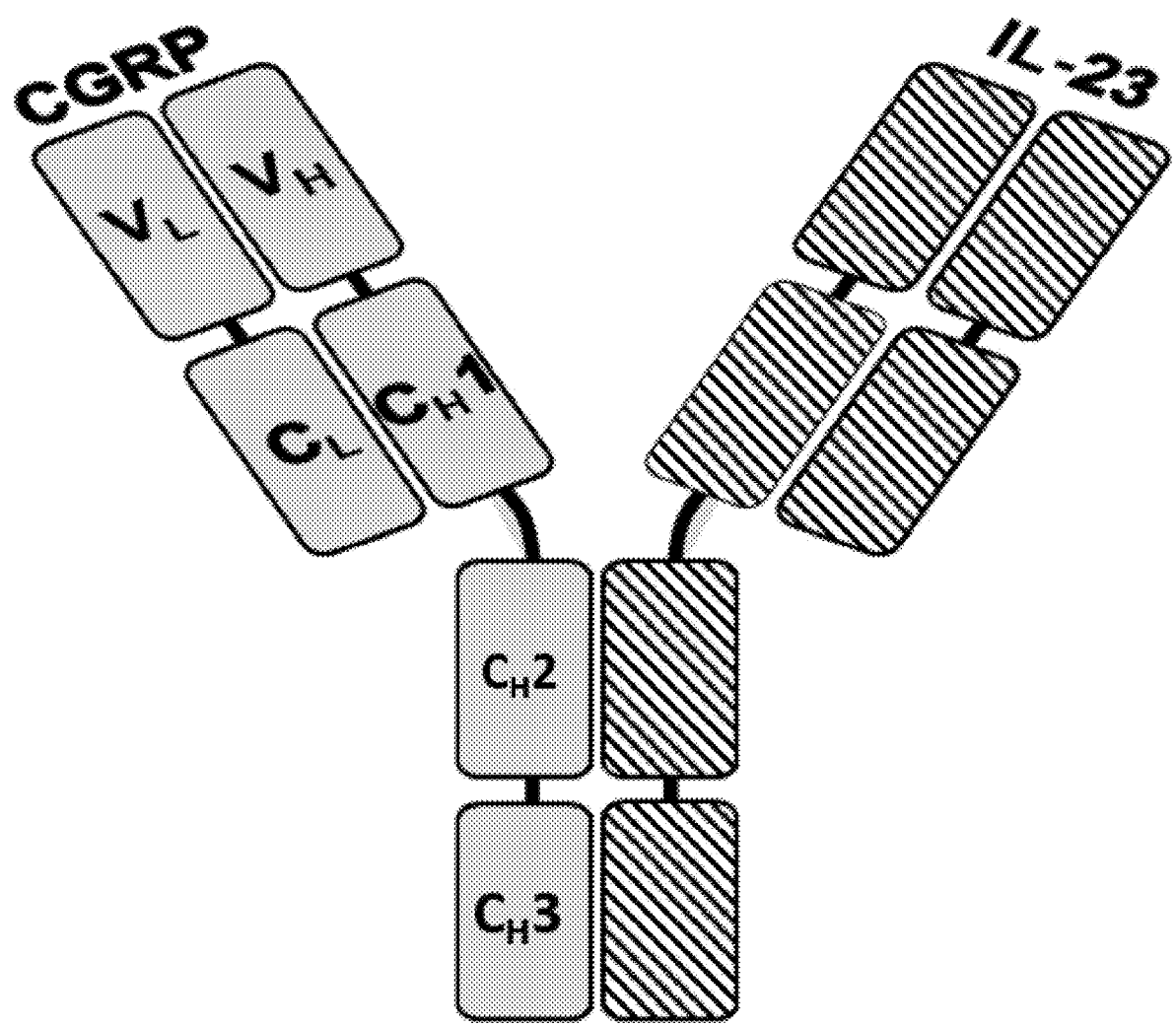

ANTI-CGRP/ANTI-IL-23 BISPECIFIC ANTIBODIES AND USES THEREOF

The present invention is in the field of medicine, particularly in the novel field of bispecific antibodies directed against Calcitonin Gene Related Peptide (CGRP) and Interleukin-23 (IL-23). The bispecific antibodies of the present invention are expected to be useful in treating autoimmune inflammatory diseases including Inflammatory Bowel Disease (IBD), such as Crohn's Disease (CD) and Ulcerative Colitis (UC), and other autoimmune diseases including Psoriatic Arthritis (PsA), ankylosing spondylitis (AS) and Atopic Dermatitis (AtD).

Autoimmune diseases arise from the body's production of an immune response against its own tissue. Autoimmune diseases are often chronic and can be debilitating and even life-threatening. IBD, which generically represents a group of disorders such as CD and UC, is a common chronic relapsing autoimmune inflammatory disease characterized pathologically by intestinal inflammation and epithelial injury. Other forms of chronic autoimmune diseases, such as PsA, AS and AtD, may affect the axial, peripheral skeleton and/or the skin.

Interleukin 23 (IL-23) is a heterodimeric cytokine believed to be important in the activation of a range of inflammatory cells required for the induction of chronic inflammation. IL-23, which is believed to be an upstream regulator of IL-6, IL-17, GM-CSF and IL-22 secretion, is composed of a p19 subunit (IL23p19) covalently paired to a p40 subunit (the p40 subunit is also shared with cytokine IL-12). Additionally, IL-23 has been implicated as playing an important role in memory/pathogenic T-cell inflammatory response as well as playing a role in the regulation of innate lymphoid cell inflammatory activity. There is evidence that IL-23 regulation of the cytokines IL-6, IL-17, GM-CSF and IL-22 is associated with inflammatory diseases including IBD, such as CD and UC, and other autoimmune diseases including psoriasis, PsA, AS and AtD.

CGRP is a 37 amino acid neuropeptide secreted by the nerves of the central and peripheral nervous systems. CGRP is widely distributed in sensory nerves, both in the peripheral and central nervous system and displays a large number of different biological activities. For instance, it is a potent vasodilator with microvasculature being sensitive thereto. When released from trigeminal and other nerve fibers, CGRP is thought to mediate its biological responses by binding to specific cell surface receptors. CGRP is believed to play a role in the modulation and/or transmission of pain signaling and in neurogenic inflammation. CGRP has been reported to play a role in migraines as CGRP is released upon stimulation of sensory nerves. The release of CGRP increases vascular permeability and subsequent plasma protein leakage (plasma protein extravasation) in tissues innervated by trigeminal nerve fibers upon stimulation of these fibers. In addition, studies have reported that infusion of CGRP in patients who suffer from migraines has resulted in migraine-like symptoms.

Current FDA approved treatments for autoimmune diseases such as IBD include corticosteroids, often used to treat acute inflammation, and bioproducts, many of which (such as REMICADE®, ENBREL® and HUMIRA) attempt to target and neutralize TNFα in the body. Another bioproduct approved for treatment of PsA includes STELARA® which attempts to target the shared p40 subunit of cytokines IL-12 and IL-23. Current treatments have demonstrated efficacy for reducing symptoms and slowing progression of some autoimmune diseases in a subset of patients. However, a large percentage of patients are nonresponsive to currently available treatments (for example, induction of remission occurs in only 30-50% of CD patients treated with TNFα neutralization, and loss of response to TNFα neutralization occurs in between 23 and 46% of patients following 12 months of treatment). Alternative therapies for autoimmune diseases include antibodies that bind to the p19 subunit of IL-23, such as those disclosed in U.S. Pat. No. 9,023,358.

While currently approved treatments for autoimmune diseases treat the inflammatory aspect of the disease, said treatments have proved ineffective in treating associated pain. Even in patients suffering from IBD (CD and UC) that are responsive to anti-TNFα therapy, pain remains. It is thought that inflammation associated with autoimmune diseases drives central sensitization to pain leading to hyperalgesia and allodynia. The consequence is that pain can be present even after inflammation has subsided with a high percentage of patients continuing to take pain medication. The standard therapies for pain in patients suffering from IBD are analgesics including NSAIDS, COX-2 inhibitors and opiates. At present, patients suffering from IBD are filling a similar number of analgesic prescriptions both prior to and post the introduction of biologic therapy. Antibodies that bind to CGRP, such as those described in U.S. Pat. No. 9,073,991, have been suggested as therapeutics for migraine.

One approach to such alternative therapies may include the co-administration of two antibodies treating different aspects of the autoimmune disease (e.g. pathology of the disease and associated pain). Co-administration requires either injections of two separate products or a single injection of a co-formulation of two different antibodies. While two injections permit flexibility of dose amounts and timing, it is inconvenient to patients both for compliance and pain. Moreover, while a co-formulation might provide some flexibility of dose amounts, it is often quite challenging or impossible to find formulation conditions having acceptable viscosity (at relatively high concentration) and that promote chemical and physical stability of both antibodies due to different molecular characteristics of the two antibodies. Additionally, co-administration and co-formulation involve the additive costs of two different drug therapies which can increase patient and/or payer costs.

Bispecific antibodies that bind to two distinct antigens have been proposed as a solution to problems associated with co-administration and/or co-formulation. Bispecific antibodies that bind to human IL-17 and human IL-23 have been described by Mabry R et al. (Protein Engineering Design and Selection, Vol. 23, No. 3, pages 115-127, 2010) but bispecific antibodies targeting human IL-23 and human CGRP do not appear to have been described previously.

Thus, there remains a need for alternative therapies for treatment of autoimmune diseases that have both disease modification and pain management properties and preferably such alternative therapies comprise a bispecific antibody.

The present invention provides an immunoglobulin G (IgG) bispecific antibody comprising a first heavy chain (HC1), a first light chain (LC1), a second heavy chain (HC2) and a second light chain (LC2), wherein HC1 forms at least one inter-chain disulfide bond with LC1, HC2 forms at least one inter-chain disulfide bond with LC2, and HC1 forms at least one inter-chain disulfide bond with HC2, and wherein the antibody binds to human calcitonin gene related peptide (CGRP) and the p19 subunit of human IL-23.

The present invention further provides an IgG bispecific antibody comprising
  a) a first heavy chain (HC1) comprising a first heavy chain variable region (HC1VR), wherein the HC1VR comprises amino acid sequences H1CDR-1, H1CDR-2, and H1CDR-3 and wherein H1CDR-1 is SEQ ID NO: 12, H1CDR-2 is SEQ ID NO: 14, and H1CDR-3 is SEQ ID NO: 16;
  b) a first light chain (LC1) comprising a light chain variable region (LC1VR), wherein the LC comprises amino acid sequences L1CDR-1, L1CDR-2, and L1 CDR-3 and wherein L1 CDR-1 is SEQ ID NO: 34, L1 CDR-2 is SEQ ID NO: 36, and L1CDR-3 is SEQ ID NO: 38;
  c) a second heavy chain (HC2) comprising a second heavy chain variable region (HC2VR) wherein the HC2VR comprises amino acid sequences H2CDR-1, H2CDR-2, and H2CDR-3 and wherein H2CDR-1 is SEQ ID NO: 23, H2CDR-2 is SEQ ID NO: 25, and H2CDR-3 is SEQ ID NO: 27; and
  d) a second light chain (LC2) comprising a second light chain variable region (LC2VR), wherein the LC2VR comprises amino acid sequences L2CDR-1, L2CDR-2, and L2CDR-3 and wherein L2CDR-1 is SEQ ID NO: 42, L2CDR-2 is SEQ ID NO: 44, and L2CDR-3 is SEQ ID NO: 46,
wherein HC1 forms at least one inter-chain disulfide bond with LC1, HC2 forms at least one inter-chain disulfide bond with LC2, and HC1 forms at least one inter-chain disulfide bond with HC2, and wherein the antibody binds to human calcitonin gene related peptide (CGRP) and the p19 subunit of human IL-23.

In a preferred embodiment of the IgG bispecific antibody of the present invention, HC1 and HC2 are human $IgG_1$ HCs, LC1 is a human kappa LC and LC2 is a human lambda light chain, wherein
  (i) HC1 has a tyrosine residue at position 39 (Kabat) of the HC1VR, a glutamine at position 105 (Kabat) of the HC1VR, a cysteine residue at position 127 (Kabat) of the HC1 $C_H1$ domain (HC1$C_H1$), an aspartic acid residue at position 228 (Kabat) of the HC1 hinge domain, a glycine residue at position 222 (Kabat) of the HC1 hinge domain, a glycine residue at position 356 (EU) of the HC1 $C_H3$ domain, an aspartic acid residue at position 357 (EU) of the HC1 $C_H3$ domain, a glutamine residue at position 364 (EU) of the HC1 $C_H3$ domain, and an alanine residue at position 407 (EU) of the HC1 $C_H3$ domain;
  (ii) HC2 has a lysine residue at position 39 (Kabat) of the HC2VR, an alanine residue at position 166 (Kabat) of the HC2 $C_H1$ domain, a glycine residue at position 170 (Kabat) of the HC2 $C_H1$ domain, a serine residue at position 349 (EU) of the HC2 $C_H3$ domain, a methionine residue at position 366 (EU) of the HC2 $C_H3$ domain, a tyrosine residue at position 370 (EU) of the HC2 $C_H3$ domain, and a valine residue at position 409 (EU) of the HC2 $C_H3$ domain;
  (iii) LC1 has an arginine residue at position 38 (Kabat) of the LC1VR, an aspartic acid residue at position 42 (Kabat) of the LC1VR, and a lysine residue at position 122 (Kabat) of the LC1 $C_L$ domain;
  (iv) LC2 has an arginine residue at position 1 (Kabat) of the LC2VR, an aspartic acid residue at position 38 of the LC2VR, a tyrosine residue at position 135 (Kabat) of the LC2 $C_L$ domain, and a tryptophan residue at position 176 (Kabat) of the LC2 $C_L$ domain.

In a still further preferred embodiment of the IgG bispecific antibody of the present invention, HC1 has an alanine residue at position 234 (Kabat) of the HC1 $C_H2$ domain and an alanine residue at position 235 (Kabat) of the HC1 $C_H2$ domain, and HC2 has an alanine residue at position 234 (Kabat) of the HC2 $C_H2$ domain and an alanine residue at position 235 (Kabat) of the HC2 $C_H2$ domain.

In a preferred embodiment of the IgG bispecific antibody of the present invention, HC1 and HC2 are human $IgG_4$ HCs, the LC1 is a human kappa LC and LC2 is a human lambda light chain, wherein
  (i) HC1 has a tyrosine residue at position 39 (Kabat) of the HC1VR, a glutamine at position 105 (Kabat) of the HC1VR, a cysteine residue at position 127 (Kabat) of the HC1 $C_H1$ domain (HC1$C_H1$), an aspartic acid residue at position 228 (Kabat) of the HC1 hinge domain, a glycine residue at position 222 (Kabat) of the HC1 hinge domain, a glycine residue at position 356 (EU) of the HC1 $C_H3$ domain, an aspartic acid residue at position 357 (EU) of the HC1 $C_H3$ domain, a glutamine residue at position 364 (EU) of the HC1 $C_H3$ domain, and an alanine residue at position 407 (EU) of the HC1 $C_H3$ domain;
  (ii) HC2 has a lysine residue at position 39 (Kabat) of the HC2VR, an alanine residue at position 166 (Kabat) of the HC2 $C_H1$ domain, a glycine residue at position 170 (Kabat) of the HC2 $C_H1$ domain, a serine residue at position 349 (EU) of the HC2 $C_H3$ domain, a methionine residue at position 366 (EU) of the HC2 $C_H3$ domain, a tyrosine residue at position 370 (EU) of the HC2 $C_H3$ domain, and a valine residue at position 409 (EU) of the HC2 $C_H3$ domain;
  (iii) LC1 has an arginine residue at position 38 (Kabat) of the LC1VR, an aspartic acid residue at position 42 (Kabat) of the LC1VR, and a lysine residue at position 122 (Kabat) of the LC1 $C_L$ domain;
  (iv) LC2 has an arginine residue at position 1 (Kabat) of the LC2VR, an aspartic acid residue at position 38 of the LC2VR, a tyrosine residue at position 135 (Kabat) of the LC2 $C_L$ domain, and a tryptophan residue at position 176 (Kabat) of the LC2 $C_L$ domain.

In a further embodiment of the IgG bispecific antibody of the present invention, the bispecific antibody comprises
  a) a first heavy chain (HC1) comprising a first heavy chain variable region (HC1VR) having the amino acid sequence of SEQ ID NO: 3;
  b) a first light chain (LC1) comprising a first light chain variable region (LC1VR) having the amino acid sequence of SEQ ID NO: 4;
  c) a second heavy chain (HC2) comprising a second heavy chain variable region (HC2VR) having the amino acid sequence of SEQ ID NO: 5; and
  d) a second light chain (LC2) comprising a second light chain variable region (LC2VR) having the amino acid sequence of SEQ ID NO: 6,
wherein HC1 forms at least one inter-chain disulfide bond with LC1, HC2 forms at least one inter-chain disulfide bond with LC2, and HC1 forms at least one inter-chain disulfide bond with HC2, and wherein the antibody binds to human CGRP and the p19 subunit of human IL-23.

In a preferred embodiment of the IgG bispecific antibody of the present invention, HC1 and HC2 are human $IgG_1$ HCs, LC1 is a human kappa LC and LC2 is a human lambda LC, wherein
  (i) HC1 has a cysteine residue at position 127 (Kabat) of the HC1 $C_H1$ domain (HC1$C_H1$), an aspartic acid residue at position 228 (Kabat) of the HC1 hinge domain, a glycine residue at position 222 (Kabat) of the HC1 hinge domain, a glycine residue at position 356 (EU) of the HC1 $C_H3$ domain, an aspartic acid residue at position 357 (EU) of the HC1 $C_H3$ domain, a glutamine residue at position 364 (EU) of the HC1 $C_H3$ domain, and an alanine residue at position 407 (EU) of the HC1 $C_H3$ domain;

(ii) HC2 has an alanine residue at position 166 (Kabat) of the HC2 $C_H1$ domain, a glycine residue at position 170 (Kabat) of the HC2 $C_H1$ domain, a serine residue at position 349 (EU) of the HC2 $C_H3$ domain, a methionine residue at position 366 (EU) of the HC2 $C_H3$ domain, a tyrosine residue at position 370 (EU) of the HC2 $C_H3$ domain, and a valine residue at position 409 (EU) of the HC2 $C_H3$ domain;

(iii) LC1 has a lysine residue at position 122 (Kabat) of the LC1 $C_L$ domain;

(iv) LC2 has a tyrosine residue at position 135 (Kabat) of the LC2 $C_L$ domain, and a tryptophan residue at position 176 (Kabat) of the LC2 $C_L$ domain.

In a still further preferred embodiment of the IgG bispecific antibody of the present invention, HC1 has an alanine residue at position 234 (Kabat) of the HC1 $C_H2$ domain and an alanine residue at position 235 (Kabat) of the HC1 $C_H2$ domain, and HC2 has an alanine residue at position 234 (Kabat) of the HC2 $C_H2$ domain and an alanine residue at position 235 (Kabat) of the HC2 $C_H2$ domain.

In a preferred embodiment of the IgG bispecific antibody of the present invention, HC1 and HC2 are human $IgG_4$ HCs, the LC1 is a human kappa LC and LC2 is a human lambda LC, wherein HC1 has a cysteine residue at position 127 (Kabat) of the HC1 $C_H1$ domain (i) ($HC1C_H1$), an aspartic acid residue at position 228 (Kabat) of the HC1 hinge domain, a glycine residue at position 222 (Kabat) of the HC1 hinge domain, a glycine residue at position 356 (EU) of the HC1 $C_H3$ domain, an aspartic acid residue at position 357 (EU) of the HC1 $C_H3$ domain, a glutamine residue at position 364 (EU) of the HC1 $C_H3$ domain, and an alanine residue at position 407 (EU) of the HC1 $C_H3$ domain;

(ii) HC2 has an alanine residue at position 166 (Kabat) of the HC2 $C_H1$ domain, a glycine residue at position 170 (Kabat) of the HC2 $C_H1$ domain, a serine residue at position 349 (EU) of the HC2 $C_H3$ domain, a methionine residue at position 366 (EU) of the HC2 $C_H3$ domain, a tyrosine residue at position 370 (EU) of the HC2 $C_H3$ domain, and a valine residue at position 409 (EU) of the HC2 $C_H3$ domain;

(iii) LC1 has a lysine residue at position 122 (Kabat) of the LC1 $C_L$ domain; and (iv) LC2 has a tyrosine residue at position 135 (Kabat) of the LC2 $C_L$ domain, and a tryptophan residue at position 176 (Kabat) of the LC2 $C_L$ domain.

In a further embodiment of the IgG bispecific antibody of the present invention, the bispecific antibody comprises
a) a first heavy chain (HC1) having the amino acid sequence of SEQ ID NO: 7;
b) a first light chain (LC1) having the amino acid sequence of SEQ ID NO: 8;
c) a second heavy chain (HC2) having the amino acid sequence of SEQ ID NO: 9; and
d) a second light chain (LC2) having the amino acid sequence of SEQ ID NO: 10,
wherein HC1 forms an inter-chain disulfide bond with LC1, HC2 forms an inter-chain disulfide bond with LC2, and HC1 forms at least one inter-chain disulfide bond with HC2, and wherein the antibody binds to human CGRP and the p19 subunit of human IL-23.

The bispecific antibodies of the present invention are thermally stable and physically stable. Moreover, bispecific antibodies of the present invention may also exhibit low aggregation. Furthermore, bispecific antibodies of the present invention may also neutralize human CGRP and human IL23p19 (the p19 subunit of IL-23), as well as simultaneously binding both ligands. The presently claimed antibodies may also avoid the challenges of finding formulation conditions that must satisfy the different molecular characteristics of two different, separate antibodies.

Furthermore, the ability to generate a bispecific antibody that binds to both human CGRP and the p19 subunit of human IL-23 with fully IgG architecture is a challenge in antibody engineering. Particular problems include LC mispairing (e.g. anti-IL-23 light chain mispairing with anti-CGRP heavy chain and/or anti-CGRP light chain mispairing with anti-IL-23 heavy chain) and half-body formation. To minimize LC mispairing and half-body formation, mutations are engineered into HC-LC pairs to create designed residues in the interface of the heavy chain-light chain variable ($V_H/V_L$) domains, the heavy chain-light chain constant ($C_H1/C_L$) domains and the heavy chain constant domains ($C_H3$). The mutations induce proper assembly of the heterodimeric bispecific antibody of the present invention into a fully IgG architecture.

Given the amino acid sequences provided herein, one of ordinary skill in the art can use this knowledge to design a DNA molecule to encode and express any IgG bispecific antibody, or fragment thereof, described hereinabove. The present invention thus encompasses all DNA sequences encoding a bispecific antibody or fragment thereof according to the invention.

In particular, the present invention provides a DNA molecule comprising a polynucleotide sequence encoding a heavy chain (HC) polypeptide comprising a HCVR having the amino acid sequence of SEQ ID NO: 3.

The present invention further provides a DNA molecule comprising a polynucleotide sequence encoding a light chain (LC) polypeptide comprising a LCVR having the amino acid sequence of SEQ ID NO: 4.

The present invention still further provides a DNA molecule comprising a polynucleotide sequence encoding a HC polypeptide comprising a HCVR having the amino acid sequence of SEQ ID NO: 5.

The present invention still further provides a DNA molecule comprising a polynucleotide sequence encoding a LC polypeptide comprising a LCVR having the amino acid sequence of SEQ ID NO: 6.

The present invention still further provides a DNA molecule comprising a polynucleotide sequence encoding a HC polypeptide having the amino acid sequence of SEQ ID NO: 7.

The present invention still further provides a DNA molecule comprising a polynucleotide sequence encoding a LC polypeptide having the amino acid sequence of SEQ ID NO: 8.

The present invention still further provides a DNA molecule comprising a polynucleotide sequence encoding a HC polypeptide having the amino acid sequence of SEQ ID NO: 9.

The present invention still further provides a DNA molecule comprising a polynucleotide sequence encoding a LC polypeptide having the amino acid sequence of SEQ ID NO: 10.

In a preferred embodiment, the polynucleotides of the present invention described hereinabove are operably linked to an expression control sequence.

The present invention provides an expression vector comprising a polynucleotide sequence encoding a HC polypeptide comprising a HCVR having the amino acid sequence of SEQ ID NO: 3 and a polynucleotide sequence encoding a LC polypeptide comprising a LCVR having the amino acid sequence of SEQ ID NO: 4, wherein the polynucleotide sequences are operably linked to an expression control sequence.

The present invention further provides an expression vector comprising a polynucleotide sequence encoding a HC polypeptide comprising a HCVR having the amino acid sequence of SEQ ID NO: 5 and a polynucleotide sequence encoding a LC polypeptide comprising a LCVR having the amino acid sequence of SEQ ID NO: 6, wherein the polynucleotide sequences are operably linked to an expression control sequence.

The present invention still further provides an expression vector comprising a polynucleotide sequence encoding a first HC polypeptide comprising a HCVR having the amino acid sequence of SEQ ID NO: 3, a polynucleotide sequence encoding a first LC polypeptide comprising a LCVR having the amino acid sequence of SEQ ID NO: 4, a polynucleotide sequence encoding a second HC polypeptide comprising a HCVR having the amino acid sequence of SEQ ID NO: 5, and a polynucleotide sequence encoding a second LC polypeptide comprising a LCVR having the amino acid sequence of SEQ ID NO: 6, wherein the polynucleotide sequences are operably linked to an expression control sequence.

The present invention provides an expression vector comprising a polynucleotide sequence encoding a HC polypeptide having the amino acid sequence of SEQ ID NO: 7 and a polynucleotide sequence encoding a LC polypeptide having the amino acid sequence of SEQ ID NO: 8, wherein the polynucleotide sequences are operably linked to an expression control sequence.

The present invention further provides an expression vector comprising a polynucleotide sequence encoding a HC polypeptide having the amino acid sequence of SEQ ID NO: 9 and a polynucleotide sequence encoding a LC polypeptide having the amino acid sequence of SEQ ID NO: 10, wherein the polynucleotide sequences are operably linked to an expression control sequence.

The present invention still further provides an expression vector comprising a polynucleotide sequence encoding a first HC polypeptide having the amino acid sequence of SEQ ID NO: 7, a polynucleotide sequence encoding a first LC polypeptide having the amino acid sequence of SEQ ID NO: 8, a polynucleotide sequence encoding a second HC polypeptide having the amino acid sequence of SEQ ID NO: 9 and a polynucleotide sequence encoding a second LC polypeptide having the amino acid sequence of SEQ ID NO: 10, wherein the polynucleotide sequences are operably linked to an expression control sequence.

The present invention provides a recombinant host cell comprising a DNA molecule comprising a polynucleotide sequence encoding a polynucleotide sequence encoding a first HC polypeptide comprising a HCVR having the amino acid sequence of SEQ ID NO: 3, a polynucleotide sequence encoding a first LC polypeptide comprising a LCVR having the amino acid sequence of SEQ ID NO: 4, a polynucleotide sequence encoding a second HC polypeptide comprising a HCVR having the amino acid sequence of SEQ ID NO: 5, and a polynucleotide sequence encoding a second LC polypeptide comprising a LCVR having the amino acid sequence of SEQ ID NO: 6, wherein the cell is capable of expressing a bispecific antibody of the present invention, wherein the first HC forms at least one inter-chain disulfide bond with the first LC, the second HC forms at least one inter-chain disulfide bond with the second LC, and the first HC forms at least one inter-chain disulfide bond with the second HC, and wherein the antibody binds to human CGRP and to the p19 subunit of human IL-23.

The present invention provides a recombinant host cell comprising a DNA molecule comprising a polynucleotide sequence encoding a first HC polypeptide having the amino acid sequence of SEQ ID NO: 7 and a polynucleotide sequence encoding a first LC polypeptide having the amino acid sequence of SEQ ID NO: 8, and a DNA molecule comprising a polynucleotide sequence encoding a second HC polypeptide having the amino acid sequence of SEQ ID NO: 9 and a polynucleotide sequence encoding a second LC polypeptide having the amino acid sequence of SEQ ID NO: 10, wherein the cell is capable of expressing a bispecific antibody of the present invention, wherein the first HC forms at least one inter-chain disulfide bond with the first LC, the second HC forms at least one inter-chain disulfide bond with the second LC, and the first HC forms at least one inter-chain disulfide bond with the second HC, and wherein the antibody binds to human CGRP and to the p19 subunit of human IL-23.

The present invention also provides a process for producing a bispecific antibody of the present invention, the process comprising cultivating a recombinant host cell of the present invention under conditions such that the bispecific antibody is expressed, and recovering the expressed bispecific antibody.

The present invention also provides a bispecific antibody according to the present invention produced by said process.

Preferably, the recombinant host cells is a mammalian host cell selected from the group consisting of CHO, NS0, HEK293 and COS cells.

The present invention provides a pharmaceutical composition, comprising a bispecific antibody of the present invention and an acceptable carrier, diluent, or excipient.

The present invention provides a method of treating inflammatory bowel disease (IBD) comprising administering to a patient in need thereof an effective amount of an IgG bispecific antibody according to the present invention.

In a preferred embodiment, the IBD is Crohn's Disease (CD).

In a further preferred embodiment, the IBD is ulcerative colitis (UC).

The present invention further provides a method of pain associated with inflammatory bowel disease (IBD) comprising administering to a patient in need thereof an effective amount of an IgG bispecific antibody according to the present invention.

In a preferred embodiment, the IBD is Crohn's Disease (CD) and the pain is associated with CD.

In a further preferred embodiment, the IBD is ulcerative colitis (UC) and the pain is associated with UC.

The present invention still further provides a method of treating psoriasis comprising administering to a patient in need thereof an effective amount of an IgG bispecific antibody according to the present invention.

The present invention still further provides a method of treating pain associated with psoriasis comprising administering to a patient in need thereof an effective amount of an IgG bispecific antibody according to the present invention.

The present invention still further provides a method of treating palmoplantar pustulosis comprising administering to a patient in need thereof an effective amount of an IgG bispecific antibody according to the present invention.

The present invention still further provides a method of treating pain associated with palmoplantar pustulosis comprising administering to a patient in need thereof an effective amount of an IgG bispecific antibody according to the present invention.

The present invention still further provides a method of treating psoriatic arthritis (PsA) comprising administering to a patient in need thereof an effective amount of an IgG bispecific antibody according to the present invention.

The present invention still further provides a method of treating pain associated with psoriatic arthritis (PsA) comprising administering to a patient in need thereof an effective amount of an IgG bispecific antibody according to the present invention.

The present invention still further provides a method of treating ankylosing spondylitis (AS) comprising administering to a patient in need thereof an effective amount of an IgG bispecific antibody according to the present invention.

The present invention still further provides a method of treating pain associated with ankylosing spondylitis (AS) comprising administering to a patient in need thereof an effective amount of an IgG bispecific antibody according to the present invention.

The present invention still further provides a method of treating atopic dermatitis (AtD) comprising administering to a patient in need thereof an effective amount of an IgG bispecific antibody according to the present invention.

The present invention still further provides a method of treating pain associated with atopic dermatitis (AtD) comprising administering to a patient in need thereof an effective amount of an IgG bispecific antibody according to the present invention.

The present invention still further provides an IgG bispecific antibody according to the present invention for use in therapy.

The present invention still further provides an IgG bispecific antibody according to the present invention, for use in the treatment of inflammatory bowel disease (IBD).

In a preferred embodiment, the IBD is Crohn's Disease (CD).

In a further preferred embodiment, the IBD is ulcerative colitis (UC).

The present invention still further provides an IgG bispecific antibody according to the present invention for use in the treatment of pain associated with inflammatory bowel disease (IBD).

In a preferred embodiment, the IBD is Crohn's Disease (CD) and the pain is associated with CD.

In a further preferred embodiment, the IBD is ulcerative colitis (UC) and the pain is associated with UC.

The present invention still further provides an IgG bispecific antibody according to the present invention for use in the treatment of psoriasis.

The present invention still further provides an IgG bispecific antibody according to the present invention for use in the treatment of pain associated with psoriasis.

The present invention still further provides an IgG bispecific antibody according to the present invention for use in the treatment of palmoplantar pustulosis.

The present invention still further provides an IgG bispecific antibody according to the present invention for use in the treatment of pain associated with palmoplantar pustulosis.

The present invention still further provides an IgG bispecific antibody according to the present invention for use in the treatment of psoriatic arthritis (PsA).

The present invention still further provides an IgG bispecific antibody according to the present invention for use in the treatment of pain associated with psoriatic arthritis (PsA).

The present invention still further provides an IgG bispecific antibody according to the present invention for use in the treatment of ankylosing spondylitis (AS).

The present invention still further provides an IgG bispecific antibody according to the present invention for use in the treatment of pain associated with ankylosing spondylitis (AS).

The present invention still further provides an IgG bispecific antibody according to the present invention for use in the treatment of atopic dermatitis (AtD).

The present invention still further provides an IgG bispecific antibody according to the present invention for use in the treatment of pain associated with atopic dermatitis (AtD).

Another embodiment of the present invention comprises use of a bispecific antibody of the present invention in the manufacture of a medicament for the treatment of autoimmune diseases.

A still further embodiment of the present invention comprises use of an IgG bispecific antibody of the present invention in the manufacture of a medicament for the treatment of inflammatory bowel disease (IBD).

In a preferred embodiment, the IBD is Crohn's Disease (CD).

In a further preferred embodiment, the IBD is ulcerative colitis (UC).

An additional embodiment of the present invention comprises use of an IgG bispecific antibody of the present invention in the manufacture of a medicament for the treatment of pain associated with inflammatory bowel disease (IBD).

In a preferred embodiment, the IBD is Crohn's Disease (CD) and the pain is associated with CD.

In a further preferred embodiment, the IBD is ulcerative colitis (UC) and the pain is associated with UC.

An additional embodiment of the present invention comprises use of an IgG bispecific antibody of the present invention in the manufacture of a medicament for the treatment of psoriasis.

An additional embodiment of the present invention comprises use of an IgG bispecific antibody of the present invention in the manufacture of a medicament for the treatment of pain associated with psoriasis.

An additional embodiment of the present invention comprises use of an IgG bispecific antibody of the present invention in the manufacture of a medicament for the treatment of palmoplantar pustulosis.

An additional embodiment of the present invention comprises use of an IgG bispecific antibody of the present invention in the manufacture of a medicament for the treatment of pain associated with palmoplantar pustulosis.

An additional embodiment of the present invention comprises use of an IgG bispecific antibody of the present invention in the manufacture of a medicament for the treatment of psoriatic arthritis (PsA).

An additional embodiment of the present invention comprises use of an IgG bispecific antibody of the present invention in the manufacture of a medicament for the treatment of pain associated with psoriatic arthritis (PsA).

An additional embodiment of the present invention comprises use of an IgG bispecific antibody of the present invention in the manufacture of a medicament for the treatment of ankylosing spondylitis (AS).

An additional embodiment of the present invention comprises use of an IgG bispecific antibody of the present invention in the manufacture of a medicament for the treatment of pain associated with ankylosing spondylitis (AS).

An additional embodiment of the present invention comprises use of an IgG bispecific antibody of the present invention in the manufacture of a medicament for the treatment of atopic dermatitis (AtD).

An additional embodiment of the present invention comprises use of an IgG bispecific antibody of the present invention in the manufacture of a medicament for the treatment of pain associated with atopic dermatitis (AtD).

BRIEF DESCRIPTION OF THE DRAWINGS

FIG. 1 illustrates the IgG architecture of the anti-CGRP and anti-IL-23 bispecific antibody of the present invention.

DEFINITIONS

When used herein the term "bispecific antibody" refers to a heterodimeric IgG molecule, or fragment thereof, namely a $F(ab')_2$ fragment, wherein each arm of the IgG antibody exhibits selective monovalent binding to its cognate antigen due to two different heavy chains and two different light chains forming the antibody. In the present invention one arm of the antibody binds human CGRP (SEQ ID NO: 1), and the other arm binds the p19 subunit of human IL-23 (SEQ ID NO: 2), as illustrated in FIG. 1.

The bispecific antibody of the present invention binds to the p19 subunit of human IL-23 but does not bind to the p40 subunit of human IL-23 that is shared with IL-12, i.e. the bispecific antibody binds to human IL-23 but does not bind to human IL-12.

The antibody of the present invention is an IgG type antibody and has "heavy" chains and "light" chains that are cross-linked via intra- and inter-chain disulfide bonds. Each heavy chain is comprised of an N-terminal HCVR and a heavy chain constant region ("HCCR"). Each light chain is comprised of a LCVR and a light chain constant region ("LCCR"). Light chains each form disulfide bonds with a heavy chain, and the two heavy chains form two disulfide bonds between each other.

The constant region of the heavy chains contains $C_H1$, hinge, $C_H2$, and $C_H3$ domains. $C_H1$ comes after the HCVR; the $C_H1$ and HCVR form the heavy chain portion of a Fab. $C_H2$ comes after the hinge region and before $C_H3$. $C_H3$ comes after $C_H2$ and is at the carboxy-terminal end of the heavy chain.

The constant region of the light chains contains one domain, $C_L$. $C_L$ comes after the LCVR; the $C_L$ and LCVR form the light chain portion of a Fab. The light chain constant region can be a kappa or lambda constant region.

A "parent antibody" or "parental antibody," as used interchangeably herein, is an antibody encoded by an amino acid sequence which is used in the preparation of one arm of the IgG of the bispecific antibody of the present invention, for example through amino acid substitutions and structural alteration. The parent antibody may be a murine, chimeric, humanized or human antibody.

The terms "Kabat numbering" or "Kabat labeling" are used interchangeably herein. These terms, which are recognized in the art, refer to a system of numbering amino acid residues which are more variable (i.e., hypervariable) than other amino acid residues in the heavy and light chains variable regions of an antibody (Kabat et al., Ann. NY Acad. Sci., Vol. 190, pages 382-93, 1971; Kabat et al., Sequences of Proteins of Immunological Interest, Fifth Edition, U.S. Department of Health and Human Services, NIH Publication No. 91-3242, 1991).

The terms "EU numbering" or "EU labeling" are used interchangeably herein. These terms, which are recognized in the art, refer to a system of numbering amino acid residues to variable and constant domains based on the International Immunogenetics Information System® available at www.imgt.org.

The terms "patient," "subject," and "individual," used interchangeably herein, refer to an animal, preferably the term refers to humans. In certain embodiments, the subject, preferably a human, is further characterized with a disease or disorder or condition (e.g., an autoimmune disorder) that would benefit from a decreased level or decreased bioactivity of both human IL-23 and human CGRP. In another embodiment the subject, preferably a human, is further characterized as being at risk of developing a disorder, disease or condition that would benefit from a decreased level or decreased bioactivity of both human IL-23 and human CGRP.

Bispecific Antibody Engineering

IgG bispecific antibodies of the present invention are heterodimeric in that each arm of the antibody exhibits selective monovalent binding to its cognate antigen due to two different heavy chains and two different light chains forming the antibody: one arm of the antibody binds human CGRP (SEQ ID NO: 1), and the other arm binds the p19 subunit of human IL-23 (SEQ ID NO: 2).

The ability to generate bispecific antibodies with fully IgG architecture has been a long-standing challenge in antibody engineering. One proposal for generating fully IgG bispecific antibodies entails co-expression of nucleic acids encoding two distinct HC-LC pairs which, when expressed, assemble to form a single antibody comprising two distinct Fabs. However, challenges with this approach remain. Specifically, the expressed polypeptides of each desired Fab must assemble with good specificity to reduce generation of mis-matched byproducts, and the resulting heterotetramer must assemble with good stability. Procedures for directing assembly of particular HC-HC pairs by introducing modifications into regions of the HC-HC interface have been disclosed in the art. (See Klein et al., mAbs, Vol. 4, No. 6, pages 1-11, 2012; Carter et al., J. Immunol. Methods, Vol. 248, pages 7-15, 2001; Gunasekaran, et al., J. Biol. Chem., Vol. 285, pages 19637-19646, 2010; Zhu et al., Protein Science, Vol. 6, pages 781-788, 1997; and Igawa et al., Protein Eng. Des. Sel., Vol. 23 pages 667-677, 2010). However, there remains a need for alternative methods and the bispecific antibodies of the present invention have been engineered to drive proper assembly thereof.

The parental anti-CGRP and anti-IL-23 antibodies have human kappa light chain constant regions. Nevertheless, it has been discovered that changing the IL-23 portion of the bispecific antibody to a lambda light chain constant region improves proper assembly of the bispecific antibodies of the present invention. Accordingly, for the bispecific antibodies of the present invention, the light chain constant region of the anti-CGRP arm of the antibody is a kappa light chain and the light chain constant region of the anti-IL-23p19 arm of the antibody is a lambda light chain.

In addition, a number of engineered mutations relative to germline reference sequences drive specific hetero-dimerization. The germline reference sequences of the parental anti-CGRP arm of the antibody and the modified parental anti-IL-23 arm (lambda light chain) are of the antibody are as follows:

Anti-CGRP heavy chain: Variable framework 1-e/JH2 and human IgG1 (allotype IGHG1*01);
Anti-CGRP light chain: Variable framework O12/JK4 and kappa constant (allotype IGKC*01);
Anti-IL-23p19 heavy chain: Variable framework 1-69/JH6 and human IgG1 (allotype IGHG1*01); and
Anti-IL-23p19 light chain: Variable framework L11/JK4 and lambda constant (allotype IGLC2*01)

The engineered mutations that drive hetero-dimerization are summarized in Table 1 hereinbelow. The numbering of amino acids applies linear numbering. Kabat/EU numbering is provided in parentheses to allow comparison across immunoglobulins with different complementarity determining region (CDR) lengths and subclass. Specifically, Kabat numbering is provided in parentheses for mutations made in the $V_H$, $V_L$, $C_H1$, hinge and $C_L$ domains and EU numbering is provided in parentheses for mutations made in the $C_H2$ and $C_H3$ domains.

TABLE 1

Engineered mutations in the bispecific antibodies of the present invention

| Anti-CGRP heavy chain | Anti-CGRP light chain | Anti-IL23 heavy chain | Anti-IL23 light chain |
|---|---|---|---|
| Linear (Kabat) numbering Mutations introduced into HCs and LCs to induce correct antibody assembly | | | |
| Q39Y (Q39Y) | Q38R (Q38R) | Q39K (Q39K) | A1R (A1R) |
| Q111R (Q105R) | K42D (K42D) | H166A (H168A) | Q38D (Q38D) |
| S133C (S127C) | D122K (D122K) | F168G (F170G) | L136Y (L135Y) |
| K220D (K228D) | | | S176W (S176W) |
| C222G (C230G) | | | |
| Linear (EU) numbering Heavy Chain ($C_H3$ domain) heterodimer design to induce correct assembly | | | |
| D358G (D356G) | | Y347S (Y349S) | |
| E359D (E357D) | | T364M (T366M) | |
| S366Q (S364Q) | | K368Y (K370Y) | |
| Y409A (Y407A) | | K407V (K409V) | |

The above-described mutations are incorporated into the sequences of the heavy chains within the $V_H$, $C_H1$, hinge and $C_H3$ domains and into the sequences of the light chains within the $V_L$ and $C_L$ domains. The $V_H$, $V_L$, hinge, $C_H1$ and $C_L$ mutations are made to favor native pairing of the requisite light chain and heavy chain pairs and disfavor light chain mispairing. The $C_H3$ mutations are made to favor heterodimeric pairing of the two distinct heavy chains and disfavor formation of homodimers.

In addition, truncation of the C-terminal of the HCs and LCs may reduce heterogeneity and improve stability. Relative to the germline reference sequences referred to hereinabove, the anti-CGRP HC may be truncated by removal of lysine at position 448 (des 448K; des 447K according to EU numbering), the anti-IL-23 HC may be truncated by removal of lysine at position 444 (des 444K; des 447K according to EU numbering), the anti-IL-23 LC may be truncated by removal of serine at position 212 (des 5212; des 5215 according to EU numbering).

Optionally, certain antibodies of the present invention contain an Fc portion which is derived from human IgG$_1$. IgG$_1$ is well known to bind to the proteins of the Fc-gamma receptor family (FcγR) as well as C1q. Interaction with these receptors can induce antibody-dependent cell cytotoxicity (ADCC) and complement-dependent cytotoxicity (CDC). Therefore, certain amino acid substitutions are introduced into IgG1 Fc for certain antibodies of the present invention to ablate immune effector function. Mutations in the $C_H2$ region of the anti-CGRP portion of the antibody may include positions 236 and 237 (234 and 235 according to Kabat numbering). The particular mutations relative to the germline reference sequences referred to hereinabove include L236A (L234A) and L237A (L235A). Mutations in the $C_H2$ region of the anti-IL-23 portion of the antibody may include positions 232 and 233 (234 and 235 according to Kabat numbering). The particular mutations relative to the germline reference sequences referred to hereinabove include L232A (L234A) and L233A (L235A).

While the engineered mutations are described level relative to the germline reference sequences referred to hereinabove, the skilled person will recognise that alternative germline sequences may be utilized provided the defined amino acids are located at the indicated positions in the final engineered IgG bispecific antibody. For instance, the bispecific antibodies of the present invention may have a different IgG$_1$ HC allotype or a IgG$_4$ HC isotype provided the following amino acids are located at the following positions according to Kabat and EU numbering in the final engineered IgG bispecific antibody:

| Anti-CGRP HC: | $V_H$ - | Y39 (Kabat), Q105 (Kabat) |
|---|---|---|
| | $C_H1$ - | C127 (Kabat) |
| | Hinge - | D228 (Kabat), C222G (Kabat) |
| | $C_H3$- | G356 (EU), D357 (EU), Q364 (EU), A407 (EU) |
| Anti-IL-23 HC: | $V_H$- | K39 (Kabat), A166 (Kabat), G170 (Kabat) |
| | $C_H3$- | S349 (EU), M366 (EU), Y370 (EU), V409 (EU) |

Similarly, the bispecific antibodies of the present invention may have a different kappa or lambda LC allotype provided the following amino acids are located at the following positions according to Kabat and EU numbering in the final engineered IgG bispecific antibody:

| Anti-CGRP LC: | $V_L$- | R38 (Kabat), D42 (Kabat) |
|---|---|---|
| | $C_L$- | K122 (Kabat) |
| Anti-IL-23 LC: | $V_L$- | R1 (Kabat), D38 (Kabat) |
| | $C_L$- | Y135 (Kabat), W176 (Kabat) |

When expressed in certain biological systems, antibodies having Fc sequences are glycosylated in the Fc region. Typically, glycosylation occurs in the Fc region of the antibody at a highly conserved N-glycosylation site. N-glycans typically attach to asparagine. Antibodies may be glycosylated at other positions as well.

The relationship of the various regions of an exemplified IgG bispecific antibody of the present invention is shown in Tables 2(a) and (b). The numbering of amino acids applies linear numbering. Kabat (for $V_H$, $V_L$, $C_H1$, hinge and $C_L$ domains) and EU (for $C_H2$ and $C_H3$ domains) numbering can be used to determine the locations of the engineered mutations in the exemplified bispecific antibody described in Tables 2(a) and (b).

TABLE 2(a)

Heavy chains amino acid sequences

| | | | Human CGRP binding arm | | | Human IL-23p19 binding arm |
|---|---|---|---|---|---|---|
| | | Region | Positions | | Regions | Positions |
| HC1VR (SEQ ID NO: 3) | H1FR-1 | (1-22) QVQLVQSGAEVKKPGSSVKVSC (SEQ ID NO: 11) | HC2VR (SEQ ID NO: 5) | H2FR-1 | (1-22) QVQLVQSGAEVKKPGSSVKVSC (SEQ ID NO: 22) |
| | H1CDR-1 | (23-35) KASGYTFGNYWMQ (SEQ ID NO: 12) | | H2CDR-1 | (23-35) KASGYPFTRYVMH (SEQ ID NO: 23) |
| | H1FR-2 | (36-49) WVRYAPGQGLEWMG (SEQ ID NO: 13) | | H2FR-2 | (36-49) WVRKAPGQGLEWMG (SEQ ID NO: 4) |
| | H1CDR-2 | (50-66) AIYEGTGKTVYIQKFAD (SEQ ID NO: 14) | | H2CDR-2 | (50-66) YINPYNDGVNYNEEFKG (SEQ ID NO: 25) |
| | H1FR-3 | (67-96) RVTITADKSTSTAYMELSSLRSEDTAVYYC (SEQ ID NO: 15) | | H2FR-3 | (67-96) RVTITADESTSTAYMELSSLRSEDTAVYYC (SEQ ID NO: 26) |
| | H1CDR-3 | (97-108) ARLSDYVSGFGY (SEQ II NO: 16) | | H2CDR-3 | (97-104) ARNWDTGL (SEQ ID NO: 27) |
| | H1FR-4 | (109-119) WGRGTTVTVSS (SEQ ID NO: 17) | | H2FR-4 | (105-115) WGQGTTVTVSS (SEQ ID NO: 28) |
| HC1CR (SEQ ID NO: 18) | H1C$_H$1 | (120-217) ASTKGPSVFPLAPCSKSTSGGTAALGCLVKDYFPEPVTVSWNSGALTSGVHTFPAVLQSSGLYSLSSVVTVPSSSLGTQTYICNVNHKPSNTKVDKKV (SEQ ID NO: 19) | HC2CR (SEQ ID NO: 29) | H2C$_H$1 | (116-213) ASTKGPSVFPLAPSSKSTSGGTAALGCLVKDYFPEPVTVSWNSGALTSGVATGPAVLQSSGLYSLSSVVTVPSSSLGTQTYICNVNHKPSNTKVDKKV (SEQ ID NO: 30) |
| | Hinge Region | (218-232) EPDSGDKTHTCPPCP (SEQ ID NO: 49) | | Hinge Region | (214-228) EPKSCDKTHTCPPCP (SEQ ID NO: 50) |
| | H1C$_H$2 | 233-342 APEAAGGPSVFLFPPKPKDTLMISRTPEVTCVVVDVSHEDPEVKFNWYVDGVEVHNAKTKPREEQYNSTYRVVSVLTVLHQDWLNGKEYKCK | | H2C$_H$2 | (229-338) APEAAGGPSVFLFPPKPKDTLMISRTPEVTCVVVDVSHEDPEVKFNWYVDGVEVHNAKTKPREEQYNSTYRVVSVLTVLHQDWLNGKEYKCK |

TABLE 2(a)-continued

Heavy chains amino acid sequences

| Human CGRP binding arm | | Human IL-23p19 binding arm | |
|---|---|---|---|
| Region | Positions | Regions | Positions |
| H1C$_H$3 | (343-448) VSNKALP APIEKTIS KAK (SEQ ID NO: 20) GQPREPQ VYTLPPSR GDMTKN QVQLTCL VKGFYPS DIAVEWE SNGQPEN NYKTTPP VLDSDGS FFLASKLT VDKSRWQ QGNVFSC SVMHEAL HNHYTQK SLSLSPG (SEQ ID NO: 21) | H2C$_H$3 | (339-444) VSNKALP APIEKTIS KAK (SEQ ID NO: 31) GQPREPQ VSTLPPSR EEMTKNQ VSLMCLV YGFYPSDI AVEWESN GQPENNY KTTPPVLD SDGSFFLY SVLTVDK SRWQQGN VFSCSVM HEALHNH YTQKSLSL SPG (SEQ ID NO: 32) |

TABLE 2(b)

Light chains amino acid sequences

| Human CGRP binding arm | | | Human IL-23p19 binding arm | | |
|---|---|---|---|---|---|
| | Region | Positions | | Regions | Positions |
| LC1VR (SEQ ID NO: 4) | L1FR-1 | (1-23) DIQMTQS PSSLSASV GDRVTITC (SEQ ID NO: 33) | LC2VR (SEQ ID NO: 6) | L2FR-1 | (1-23) RIQMTQSP SSLSASVG DRVTITC (SEQ ID NO: 41) |
| | L1CDR-1 | (24-34) RASKDISK YLN (SEQ ID NO: 34) | | L2CDR-1 | (24-34) KASDHIG KFLT (SEQ ID NO: 42) |
| | L1FR-2 | (35-48) WYQRKPG DAPKLLI (SEQ ID NO: 35) | | L2FR-2 | (35-48) WYQDKPG KAPKLLI (SEQ ID NO: 43) |
| | L1CDR-2 | (49-56) YYTSGYH S (SEQ ID NO: 36) | | L2CDR-2 | (49-56) YGATSKL T (SEQ ID NO: 44) |
| | L1FR-3 | (57-88) GVPSRFSG SGSGTDFT LTISSLQP EDFATYY C (SEQ ID NO: 37) | | L2FR-3 | (57-88) GVPSRFSG SGSGTDFT LTISSLQP EDFATYY C (SEQ ID NO: 45) |
| | L1CDR-3 | (89-97) QQGDALP PT (SEQ ID NO: 38) | | L2CDR-3 | (89-97) QQYWSTP FT (SEQ ID NO: 46) |
| | L1FR-4 | (98-107) FGGGTKV EIK (SEQ ID NO: 39) | | L2FR-4 | (98-107) FGGGTKV EIK (SEQ ID NO: 47) |
| LC1CR | | (108-214) RTVAAPSVFIFPPSKEQL KSGTASVVCLLNNFYP REAKVQWKVDNALQS | LC2CR | | (108-212) GQPKAAPSVTLFPPSSE ELQANKATLVCYISDFY PGAVTVAWKADSSPVK |

TABLE 2(b)-continued

Light chains amino acid sequences

| Human CGRP binding arm | | Human IL-23p19 binding arm | |
|---|---|---|---|
| Region | Positions | Regions | Positions |
| | GNSQESVTEQDSKDST YSLSSTLTLSKADYEKH KVYACEVTHQGLSSPV TKSFNRGEC (SEQ ID NO: 40) | | AGVETTTPSKQSNNKY AAWSYLSLTPEQWKSH RSYSCQVTHEGSTVEKT VAPTEC (SEQ ID NO: 48) |

Bispecific Antibody Binding and Activity

The bispecific antibodies of the present invention bind both human CGRP and human IL23p19 and neutralize at least one human CGRP bioactivity and at least one human IL-23 bioactivity in vitro or in vivo. The bispecific antibodies of the present invention are inhibitors of human IL-23 in the presence and absence of human CGRP in vitro. The bispecific antibodies of the present invention are inhibitors of human CGRP in the presence or absence of human IL-23 in vitro.

The exemplified bispecific antibody of the present invention (Antibody 1) is characterized as having a binding affinity ($K_D$) for human CGRP in the range of 7.1±3.8 pM and human IL23p19 in the range of 0.6±0.1 nM at 37° C.

The bispecific antibodies of the present invention effectively neutralize CGRP and this neutralization is not affected by the presence of saturating amounts of human IL-23. The bispecific antibodies of the present invention effectively neutralize human IL-23 and this neutralization is not affected by the presence of saturating amounts of human CGRP.

Bispecific Antibody Expression

An isolated DNA encoding a HCVR region can be converted to a full-length heavy chain gene by operably linking the HCVR-encoding DNA to another DNA molecule encoding heavy chain constant regions. The sequences of human, as well as other mammalian, heavy chain constant region genes are known in the art. DNA fragments encompassing these regions can be obtained e.g., by PCR amplification.

An isolated DNA encoding a LCVR region may be converted to a full-length light chain gene by operably linking the LCVR-encoding DNA to another DNA molecule encoding a light chain constant region. The sequences of human, as well as other mammalian, light chain constant region genes are known in the art. DNA fragments encompassing these regions can be obtained by PCR amplification. The light chain constant region can be a kappa or lambda constant region. Preferably, for antibodies of the present invention, the light chain constant region of the anti-CGRP portion of the antibody is a kappa light chain and the light chain constant region of the anti-IL-23 portion of the antibody is a lambda light chain.

The polynucleotides of the present invention are expressed in a host cell after the sequences have been operably linked to an expression control sequence. Expression vectors capable of direct expression of genes to which they are operably linked are well known in the art. Expression vectors can encode a signal peptide that facilitates secretion of the polypeptide(s) from a host cell. The signal peptide can be an immunoglobulin signal peptide or a heterologous signal peptide. The expression vectors are typically replicable in the host organisms either as episomes or as an integral part of the host chromosomal DNA. Commonly, expression vectors will contain selection markers, e.g., tetracycline, neomycin, and dihydrofolate reductase, to permit detection of those cells transformed with the desired DNA sequences.

The first HC polypeptide chain (anti-CGRP) and the first LC polypeptide chain (anti-CGRP) may be expressed independently from different promoters to which they are operably linked in one vector or, alternatively, the first HC and LC polypeptide chains (anti-CGRP) may be expressed independently from different promoters to which they are operably linked in two vectors—one expressing the first HC polypeptide chain (anti-CGRP) and one expressing the first LC polypeptide chain (anti-CGRP). Similarly, the second HC polypeptide chain (anti-IL-23) and the second LC polypeptide chain (anti-IL-23) may be expressed independently from different promoters to which they are operably linked in one vector or, alternatively, the second HC and LC polypeptide chains (anti-IL-23) may be expressed independently from different promoters to which they are operably linked in two vectors—one expressing the second HC polypeptide chain (anti-IL-23) and one expressing the second LC polypeptide chain (anti-IL-23)

A host cell includes cells stably or transiently transfected, transformed, transduced or infected with one or more expression vectors expressing a first HC polypeptide chain, a first LC polypeptide chain, a second HC polypeptide chain and a second LC polypeptide chain. Creation and isolation of host cell lines producing a bispecific antibody of the invention can be accomplished using standard techniques known in the art. Mammalian cells are preferred host cells for expression of bispecific antibodies. Particular mammalian cells are HEK 293, NS0, DG-44, and CHO. Preferably, the bispecific antibodies are secreted into the medium in which the host cells are cultured, from which the bispecific antibodies can be recovered or purified.

It is well known in the art that mammalian expression of antibodies results in glycosylation. Typically, glycosylation occurs in the Fc region of the antibody at a highly conserved N-glycosylation site. N-glycans typically attach to asparagine. By way of example, the HC of the CGRP arm of the exemplified bispecific antibody presented in Table 2(a) is glycosylated at N299 (N297 according to EU numbering) and the HC of the IL-23 arm of the exemplified bispecific antibody presented in Table 2(a) is glycosylated at N295 (N297 according to EU numbering).

Medium, into which a bispecific antibody has been secreted, may be purified by conventional techniques. For example, the medium may be applied to and eluted from a Protein A or G column using conventional methods. Soluble aggregate and multimers may be effectively removed by common techniques, including size exclusion, hydrophobic interaction, ion exchange, or hydroxyapatite chromatography. The product may be immediately frozen, for example at −70° C., refrigerated, or may be lyophilized. Various methods of protein purification may be employed and such methods are known in the art and described, for example, in Deutscher, Methods in Enzymology 182: 83-89 (1990) and Scopes, Protein Purification: Principles and Practice, 3rd Edition, Springer, NY (1994).

Therapeutic Uses

As used herein, "treatment" and/or "treating" are intended to refer to all processes wherein there may be a slowing, interrupting, arresting, controlling, or stopping of the progression of the disorders described herein, but does not necessarily indicate a total elimination of all disorder symptoms. Treatment includes administration of a bispecific antibody of the present invention for treatment of a disease or condition in a mammal, particularly in a human, that would benefit from a decreased level of CGRP and/or IL-23 or decreased bioactivity of CGRP and/or IL-23, and includes: (a) inhibiting further progression of the disease, i.e., arresting its development; and (b) relieving the disease, i.e., causing regression of the disease or disorder or alleviating symptoms or complications thereof.

The bispecific antibody of the present invention is expected to treat autoimmune diseases, including autoimmune inflammatory diseases such as inflammatory bowel disease (Crohn's Disease and ulcerative colitis), and other autoimmune diseases including psoriatic arthritis, ankylosing spondylitis and atopic dermatitis.

Pharmaceutical Composition

An IgG bispecific antibody of the invention can be incorporated into a pharmaceutical composition suitable for administration to a patient. An IgG bispecific antibody of the invention may be administered to a patient alone or with a pharmaceutically acceptable carrier and/or diluent in single or multiple doses. Such pharmaceutical compositions are designed to be appropriate for the selected mode of administration, and pharmaceutically acceptable diluents, carrier, and/or excipients such as dispersing agents, buffers, surfactants, preservatives, solubilizing agents, isotonicity agents, stabilizing agents and the like are used as appropriate. Said compositions can be designed in accordance with conventional techniques disclosed in, e.g., *Remington*, The Science and Practice of Pharmacy, 22$^{nd}$ Edition, Loyd V, Ed., Pharmaceutical Press, 2012, which provides a compendium of formulation techniques as are generally known to practitioners. Suitable carriers for pharmaceutical compositions include any material which, when combined with a bispecific antibody of the invention, retains the molecule's activity and is non-reactive with the patient's immune system. A pharmaceutical composition of the present invention comprises an IgG bispecific antibody and one or more pharmaceutically acceptable carriers, diluents or excipients.

A pharmaceutical composition comprising an IgG bispecific antibody of the present invention can be administered to a patient at risk for or exhibiting diseases or disorders as described herein using standard administration techniques.

A pharmaceutical composition of the invention contains an "effective" amount of an IgG bispecific antibody of the invention. An effective amount refers to an amount necessary (at dosages and for periods of time and for the means of administration) to achieve the desired therapeutic result. An effective amount of the IgG bispecific antibody may vary according to factors such as the disease state, age, sex, and weight of the individual, and the ability of the antibody or antibody portion to elicit a desired response in the individual. An effective amount is also one in which any toxic or detrimental effect of the IgG bispecific antibody, are outweighed by the therapeutically beneficial effects.

EXAMPLES

The following Example further illustrates the invention. It is understood, however, that the Example is set forth by way of illustration and not limitation, and that various modifications may be made by one of ordinary skill in the art.

Production of Bispecific Antibodies

Bispecific Antibody 1 comprises two heavy chains and two light chains, wherein a first heavy chain has the amino acid sequence given by SEQ ID NO:7, a first light chain has the amino acid sequence given by SEQ ID NO:8, a second heavy chain has the amino acid sequence given by SEQ ID NO:9, and a second light chain has the amino acid sequence given by SEQ ID NO:10. Bispecific Antibody 1 can be made and purified as follows.

An appropriate host cell, such as HEK 293 or CHO, is either transiently or stably transfected with an expression system for secreting bispecific antibodies using an optimal predetermined HC:LC vector ratio or a single vector system encoding both heavy chains (SEQ ID NOs:7 and 9) and light chains (SEQ ID NOs: 8 and 10). Clarified media, into which the antibody has been secreted, is purified using any of many commonly-used techniques. For example, clarified medium, into which the exemplified Bispecific Antibody 1 has been secreted, is applied to a Protein A affinity column that has been equilibrated with a compatible buffer such as 20 mM TRIS (pH 8.0). The column is washed with 20 mM Tris (pH 7.0) to remove nonspecific binding components followed by a high salt wash to further remove nonspecific components. The column is equilibrated back into 20 mM Tris (pH7.0) and then the bound bispecific antibody is eluted, for example, by pH step or gradient such as 20 mM citrate (pH 3.0) and neutralized with Tris (pH 8) buffer. The Bispecific Antibody 1 is detected by absorbance at 280 nm and collected accordingly. Characterization of the Protein-A captured material shows low LC mis-assembly (2%) and low HMW polymer (4%). Misassembled Bispecific Antibody 1, soluble aggregate, and multimers may be effectively removed by common techniques including hydrophobic interaction chromatography. For instance, the levels of LC mis-assembly and low HMW polymer formation are reduced to 0.6% and 1%, respectively, by use of a second purification column using hydrophobic-interaction chromatography. Bispecific Antibody 1 is concentrated and/or sterile filtered using common techniques. The purity of Bispecific Antibody 1 after these chromatography steps is greater than 98.0% (monomer). Bispecific Antibody 1 may be immediately frozen at −70° C. or stored at 4° C. for several months.

Bispecific Antibody 1 Binding Affinity to Human IL-23 and Human CGRP

Affinity and kinetics of Bispecific Antibody 1 to human, cynomolgus monkey, mouse, rat, and rabbit IL-23 are measured using a Biacore T200 instrument (BIAcore® AB, Upsala, Sweden). Briefly, a protein-A coupled CM5 chip is generated using standard amine-coupling protocols. Bispecific Antibody 1 is diluted to 1 μg/mL in running buffer, and approximately 100 RU is captured to the chip surface. A concentration series of each ligand is injected over all flow cells at 100 μL/minute for 180 seconds followed by a 900 second dissociation phase followed by chip regeneration. Data is analyzed in Biacore T200 Evaluation Software Version 1.0 by flow-cell 1 reference subtraction along with 0 nM blank subtraction. Human, cynomolgus monkey, and rabbit IL-23 data are fit globally using a "1:1 (Langmuir) Binding" binding model to determine the on-rate ($k_{on}$) and off-rate ($k_{off}$) for each ligand. The affinity ($K_D$) is calculated from the binding kinetics according to the relationship $K_D = k_{off}/k_{on}$. Mouse IL-23 binding data is fit using a "Steady State Affinity" binding model to determine affinity ($K_D$). Stoichiometry of binding is calculated according to the relationship: Stoichiometry of binding is calculated according to the relationship: Stoichiometry=[$RU_{max}$/$RU_{Bispecific\ Antibody\ 1}$]/[$MW_{antigen}$/$MW_{Bispecific\ Antibody\ 1}$] where $MW_{antigen}$ is the molecular weight of human IL-23 and $MW_{Bispecific\ Antibody\ 1}$ is 150 kDa.

IL-23 from various species produces a concentration-dependent binding response with Bispecific Antibody 1. Table 3(a) summarizes the on-rate ($k_{on}$), off-rate ($k_{off}$), affinity ($K_D$), and stoichiometry of Bispecific Antibody 1 to various IL-23 molecules. Bispecific Antibody 1 shows similar affinities to human and cynomolgus monkey IL-23. Bispecific Antibody 1 shows very weak to no affinity for mouse, rat, and rabbit IL-23. The $K_D$ of Bispecific Antibody 1 for human IL-23 is $0.6 \pm 0.1 \times 10^{-9}$ M at 37° C. (n=4), for cynomolgus monkey IL-23 is $1.3 \pm 0.1 \times 10^{-9}$ M at 37° C. (n=2), for mouse IL-23 is $>100 \times 10^{-9}$ M at 37° C. (n=2), for rat IL-23 no discernable binding is observed at 37° C., and for rabbit IL-23 is $1,016 \times 10^{-9}$ M at 37° C.

Affinity and kinetics of Bispecific Antibody 1 to human/cynomolgus monkey, mouse/rat, and rabbit CGRP are measured using a Biacore T100 or T200 instrument (BIAcore® AB, Upsala, Sweden). Briefly, a protein-A coupled CM5 chip is generated using standard amine-coupling protocols. For CGRP affinities and kinetics, Bispecific Antibody 1 is diluted to 20 μg/mL in running buffer, and approximately 1000-1600 RU are captured on the chip surface. A concentration series of each ligand is injected over all flow cells at 70-100 μL/minute for 180 seconds followed by a 1500-1800 second dissociation phase followed by chip regeneration.

All affinity and kinetic measurements are obtained at 37° C. Data is analyzed by flow-cell 1 reference subtraction along with 0 nM blank subtraction. The on-rate ($k_{on}$) and off-rate ($k_{off}$) for each ligand are fit globally using a "1:1 (Langmuir) Binding" binding model. The affinity ($K_D$) is calculated from the binding kinetics according to the relationship $K_D = k_{off}/k_{on}$. Stoichiometry of binding is calculated according to the relationship: Stoichiometry=[$RU_{max}$/$RU_{Bispecific\ Antibody\ 1}$]/[$MW_{antigen}$/$MW_{Bispecific\ Antibody\ 1}$] where $MW_{antigen}$ is the molecular weight of human CGRP and $MW_{Bispecific\ Antibody\ 1}$ is 150 kDa.

CGRP from various species produces a concentration-dependent binding response with Bispecific Antibody 1. Table 3(b) summarizes the on-rate ($k_{on}$), off-rate ($k_{off}$), and affinity ($K_D$) of Bispecific Antibody 1 to various CGRP molecules. Bispecific Antibody 1 shows strong affinity for human/cynomolgus monkey, and rabbit CGRP but slightly weaker affinity to mouse/rat. The $K_D$ of Bispecific Antibody 1 for human/cynomolgus monkey CGRP is $7.1 \pm 3.8 \times 10^{-12}$ M at 37° C. (n=3), for mouse/rat CGRP is $169 \times 10^{-12}$ M at 37° C., and for rabbit CGRP is $21 \times 10^{-12}$ M at 37° C.

TABLE 3(a)

In Vitro binding parameters of Bispecific Antibody 1 to Human, Cynomolgus Monkey, Mouse, Rat, and Rabbit IL-23

| Species | On Rate ($k_{on}$) ($M^{-1}s^{-1}$) (±SEM) | Off Rate ($k_{off}$) ($s^{-1}$) (±SEM) | Affinity ($K_D$) (M)[a] (±SEM) | Stoichiometry (±SEM) |
|---|---|---|---|---|
| Human (n = 4) | $5.3 \pm 0.7 \times 10^5$ | $3.2 \pm 0.1 \times 10^{-4}$ | $0.6 \pm 0.1 \times 10^{-9}$ | $1.1 \pm 0.04$ |
| Cynomolgus Monkey (n = 2) | $2.8 \pm 0.1 \times 10^4$ | $3.7 \pm 0.2 \times 10^{-4}$ | $1.3 \pm 0.1 \times 10^{-9}$ | $1.0 \pm 0.1$ |
| Mouse (n = 2) | SS[b] | SS[b] | $>100 \times 10^{-9}$ | SS[b] |
| Rat (n = 1) | | No Binding observed up to 100 nM | | |
| Rabbit (n = 1) | $1.7 \times 10^4$ | $1.8 \times 10^{-2}$ | $1,016 \times 10^{-9}$ | 1.0 |

Measured by Surface Plasmon Resonance (SPR) at 37° C.

[a]Calculated as $K_D = k_{off}/k_{on}$.

[b]SS: Steady-state equilibrium model. Unable to fit kinetic parameters or stoichiometry.

TABLE 3(b)

In Vitro Binding Parameters of Bispecific Antibody 1 to
Human/Cynomolgus Monkey, Mouse/Rat, and Rabbit CGRP

| Species | On Rate ($k_{on}$) ($M^{-1s-1}$) (±SEM) | Off Rate ($k_{off}$) ($s^{-1}$) (±SEM) | Affinity ($K_D$) $(M)^a$ (±SEM) | Stoichiometry (±SEM) |
|---|---|---|---|---|
| Human/Cyno (n = 3) | $1.5 \pm 0.57 \times 10^7$ | $7.2 \pm 2.9 \times 10^{-5}$ | $7.1 \pm 3.8 \times 10^{-12}$ | $1.0 \pm 0.01$ |
| Mouse/Rat (n = 1) | $5.7 \times 10^6$ | $9.7 \times 10^{-4}$ | $169 \times 10^{-12}$ | 0.8 |
| Rabbit (n = 1) | $2.3 \times 10^7$ | $4.7 \times 10^{-4}$ | $21 \times 10^{-12}$ | 0.9 |

Measured by Surface Plasmon Resonance (SPR) at 37° C.
$^a$Calculated as $K_D = k_{off}/k_{on}$.

Simultaneous Binding of Human CGRP and Human IL-23

To test whether Bispecific Antibody 1 can simultaneously bind both human CGRP and human IL-23, a BIAcore experiment is conducted where a saturating amount of one ligand is bound to the captured bispecific antibody and then the second ligand is injected to test for binding. As the intensity of the SPR signal is dependent on molecular weight and not molarity, the magnitude of the response from the two ligands is expected to be very different (15-fold; human CGRP is approximately 4 kDa while human IL-23 is approximately 60 kDa).

A BIAcore 3000 instrument (GE Healthcare Life Sciences) is used to determine if Bispecific Antibody 1 can bind to human IL-23 and human CGRP simultaneously. A CM5 chip (Biacore P/N BR-1005-30) is prepared using manufacture's EDC/NHS amine coupling method (Biacore P/N BR-1000-50). Briefly, the surfaces of all four flow cells are activated by injecting a 1:1 mixture of EDC/NHS for 7 minutes at 10 µL/minute. Protein A (Calbiochem P/N 539202) is diluted to 50 µg/mL in 10 mM acetate, pH 4.5 buffer and immobilized to approximately 1300 RU onto all 4 flow cells by 3-minute injection at flow rate of 10 µL/minute. Unreacted sites are blocked with a 7 minute injection of ethanolamine at 10 µL/minute. Ten 30 second injections of glycine pH-1.5 at 10 µL/minute are used to remove any non-covalently associated protein and condition the chip. Running buffer is 10 mM HEPES, pH7.4, 150 mM sodium chloride, 3 mM EDTA, 0.05% polysorbate 20 (Biacore P/N BR-1006-69).

Bispecific Antibody 1 is diluted to 2 µg/mL in running buffer and approximately 1200 RU is captured on flow cell (Fc) 2 ($RU_{Bispecific\ Antibody\ 1}$). Human CGRP is diluted to 40 nM in running buffer and then two-fold serially diluted in running buffer to 10 nM. Human IL-23 is diluted to 150 nM in running buffer. Human CGRP dilutions are injected sequentially in increasing concentrations to block all human CGRP binding sites on Bispecific Antibody 1. Human IL-23 is injected immediately following human CGRP injections. Data are analyzed by flow-cell 1 reference subtraction. To ensure human CGRP binding sites are saturated, stoichiometry of binding is calculated according to the relationship:

Stoichiometry=[$RU_{CGRP}/RU_{Bispecific\ Antibody\ 1}$]/[$MW_{CGRP}/MW_{antibody}$] where MW of human CGRP and antibody is 3.8 kDa and 150 kDa respectively. The binding measurements are obtained at 25° C.

Stoichiometry and lack of increasing SPR signal with increasing concentration of human CGRP confirms that all binding sites on Bispecific Antibody 1 are saturated. Subsequent injection of human IL-23 produces a binding response demonstrating Bispecific Antibody 1 simultaneously binds both ligands. Table 4 summarizes Bispecific Antibody 1 binding to human IL-23 after human CGRP saturation. With increasing concentrations of human CGRP, no additional binding is observed after 20 nM injection indicating all available binding sites are occupied. After CGRP injections, stoichiometry of human CGRP-to-Bispecific Antibody 1 is 0.8 indicating human CGRP binding sites on Bispecific Antibody 1 are at or very near saturation. Subsequent injection of human IL-23 produces a binding response consistent with Bispecific Antibody 1 simultaneously binding both human CGRP and human IL-23 ligands.

TABLE 4

Simultaneous in vitro binding of human IL-23 to exemplified bispecific antibody
pre-saturated with human CGRP by Surface Plasmon Resonance (SPR) at 25° C.

| Bispecific Antibody 1 Bound (RU) | 10 nM human CGRP Response (RU) | 20 nM human CGRP Response (RU) | 40 nM human CGRP Response (RU) | 150 nM human IL-23 Response (RU) |
|---|---|---|---|---|
| 1220 | 19 | 23 | 23 | 331 |

Bispecific Antibody 1 does not Bind to Human IL-12, Human IL-27, or Human IL-35

Human IL-23 is a disulfide linked heterodimeric cytokine composed of a p19 subunit and a p40 subunit. Together with human IL-12, human IL-27 and human IL-35, human IL-23 is part of the IL-12 family of cytokines and shares the p40 subunit and one receptor subunit with IL-12. A BIAcore biosensor 2000 is used to demonstrate that Bispecific Antibody 1 does not bind to human IL-12, human IL-27 or human IL-35.

A capture protein (Protein A, Calbiochem) is coupled via free amine groups to carboxyl groups on flow cells 1, 2, 3 and 4 of a CM5 biosensor chip (GE Healthcare) using a mixture of N-ethyl-N-(dimethylaminopropyl)-carbodiimide (EDC) and N-hydroxysuccinimide (NETS). Flow cells are monitored with a flow rate of 30 µL/minute using a buffer containing 0.01 M HEPES, pH 7.4, 150 mM NaCl, 0.005% surfactant P20. Bispecific Antibody 1 is captured on flow cells 2, 3 and 4 to yield a total of 100 to 150 response units (RU; results reflect flow cell 2, 3 or 4 minus flow cell 1). Binding tests are followed by a regeneration step using glycine-HCl (pH 1.5) between each cycle. Flow cell 1 is used as a control to monitor non-specific binding of the analytes tested. Bispecific Antibody 1 is tested 2 times each with human IL-12, human IL-27 or human IL-35 (all at 400 nM).

Bispecific Antibody 1 does not measurably bind to human IL-12, human IL-27 or human IL-35 (all tested at 400 nM which is approximately 40× a saturating concentration of IL-23).

Bispecific Antibody 1 Solubility and Stability Analysis

Solubility

Bispecific Antibody 1 is dialyzed into 10 mM Citrate, pH 6 with and without 150 mM NaCl (abbreviated C6 and C6N respectively). Samples are concentrated to either 50 or approximately 100 mg/mL by centrifugation through a molecular weight filter (Amicon 30 kDa ultrafiltration filter, Millipore catalog # UFC903024). To a portion of both samples, Tween-80 is added to a final concentration of 0.02% (v/v; further abbreviated as C6T and C6NT respectively). Select formulations are analyzed for solubility, freeze-thaw stability, and storage stability under refrigerated and room temperature conditions.

Bispecific Antibody 1 could be concentrated to at least 131 mg/mL or 176 mg/mL in C6 and C6N formulations, respectively. After concentrating as described above, the samples are visually inspected at room temperature for precipitation or phase separation and subsequently stored for one week at 4° C. in the dark and visually re-inspected. This procedure is repeated on the same samples after storing for one additional week at −5° C. and then for an additional week at −10° C. (note due to the level of dissolved substances the samples do not freeze). The results of the solubility analysis are shown in Table 5(a). Bispecific Antibody 1 showed no visual precipitation or phase separation in either formulation or storage temperatures.

TABLE 5(a)

Solubility of Bispecific Antibody 1

| Formulation | Initial (~25° C.) | After 1 wk at 4° C. | After 1 wk at −5° C. | After 1 wk at −10° C. |
|---|---|---|---|---|
| 131 mg/mL in C6 | Clear | Clear | Clear | Clear |
| 176 mg/mL in C6N | Clear | Clear | Clear | Clear |

Chemical Stability

Chemical stability is characterized at 1 mg/ml over pH 4-7 at one pH unit intervals. These samples are stressed at 4, 25 and 40° C. for 4 weeks and degradation quantitated by SEC, CEX, and LC-MS. Chemical stability is found to be optimal at pH 6. LC-MS on the pH 6 sample after 4 wk at 40° C. identifies low level degradation within the CDRs. Specifically, 1.1% oxidation within the anti-CGRP HC (SEQ ID NO: 7) at either the Tryptophan 33 (Trp33), Methionine 34 (Met34) or Tryptophan 36 (Trp36) residue(s) and 3.9% isomerization/racemization within the anti-IL-23 HC (SEQ ID NO: 9) at the aspartic acid 56 (Asp56) is observed.

Freeze-Thaw Stability

Bispecific Antibody 1 is tested for freeze-thaw stability at high concentration. A 50 and 100 mg/mL formulation in C6T and C6NT are subjected to three slow freeze thaw cycles. The rate of freezing and thawing is controlled to mimic what would occur in a larger manufacturing container. A shelf lyophilizer under no vacuum is used to control the temperature cycle shown in Table 5(b).

TABLE 5(b)

Freeze and thaw rates used in slow freeze-thaw study of Bispecific Antibody 1

| Step | Target Temperature (° C.) | Temperature change rate (° C./min) | Hold time at Temperature (min) |
|---|---|---|---|
| 1 | 5 | 1.0 | 10 |
| 2 | −1 | 0.05 | 750 |
| 3 | −30 | 0.2 | 1 |
| 4 | −70 | 1.0 | 60 |
| 5 | −30 | 1.0 | 1 |
| 6 | −1 | 0.2 | 1000 |
| 7 | 0.5 | 0.2 | 1 |
| 8 | 15 | 1 | 1 |

After three cycles the material is analyzed by size exclusion chromatography (SEC) for high molecular weight (HMW) polymer formation and by light obscuration for particles greater than 10 micron using an AccuSizer 780 SIS (Particle Sizing Systems). Results are shown in Table 5(c). Bispecific Antibody 1 consistently shows a low percentage of HMW polymer and low particle increase under all conditions tested.

TABLE 5(c)

Stability of Bispecific Antibody 1 against three slow freeze-thaw cycles

| Formulation | % HMW increase | Particle Count/mL (≥10 micron) |
|---|---|---|
| 50 mg/mL in C6T | 0.6 | 787 |
| 50 mg/mL in C6NT | 0.2 | 833 |
| 100 mg/mL in C6T | 0.8 | nd |
| 100 mg/mL in C6NT | 0.4 | nd | nd = not determined

Refrigerated and Room Temperature Stability

Refrigerated and room temperature stability under a generic Drug Product (DP) formulation, 10 mM citrate, 0.02% Tween-80, pH 6.0 with and without 150 mM NaCl (abbreviated C6T and C6NT respectively) is evaluated by SEC and particle counting following two- and four-week static hold time. Results are shown in Tables 5(d) and (e), respectively. Data demonstrates that Bispecific Antibody 1 has low soluble (% HMW) and insoluble (≥10 micron particle count) increase following incubation.

TABLE 5(d)

Stability of Bispecific Antibody 1 at 50 mg/mL, HMW formation

| Formulation, Incubation | % HMW increase follow 4° C. storage | % HMW increase follow 25° C. storage |
|---|---|---|
| 2 wk in C6T | −0.5 | 0.1 |
| 4 wk in C6T | −0.2 | 0.1 |
| 2 wk in C6NT | −0.4 | 0.0 |
| 4 wk in C6NT | −0.4 | 0.4 |

TABLE 5(e)

Stability of Bispecific Antibody 1 at 50 mg/mL, micron size particle formation

| Formulation, Incubation | ≥10 micron particles/mL follow 25° C. storage |
|---|---|
| 2 wk in C6T | 218 |
| 4 wk in C6T | 202 |

TABLE 5(e)-continued

Stability of Bispecific Antibody 1 at 50 mg/mL, micron size particle formation

| Formulation, Incubation | ≥10 micron particles/mL follow 25° C. storage |
|---|---|
| 2 wk in C6NT | 111 |
| 4 wk in C6NT | 131 |

Viscosity

Viscosity of Bispecific Antibody 1 is analyzed at 100 mg/mL in four formulations (C6, C6N, C6T, and C6NT) at room temperature. Measurements are made on an m-VROC (Rheosense) using a shear rate of 1000 sec$^{-1}$ at 25° C. Results are shown in Table 5(f) and illustrate low viscosity for Bispecific Antibody 1 in 150 mM salt containing formulations (C6N and C6NT).

TABLE 5(f)

Solution viscosity of 100 mg/mL Bispecific Antibody 1 at room temperature in various formulations

| C6 | C6N | C6T | C6NT |
|---|---|---|---|
| 9.8 cP | 4.5 cP | 14.4 cP | 5.4 cP |

Photostability

Photostability of Bispecific Antibody 1 is characterized at 50 mg/mL protein concentration under one formulation condition (C6NT). This formulation is exposed to 20% of the International Conference on Harmonization (ICH) Expert Working Group recommend exposure level (Q1B-Stability Testing: Photostability Testing of New Drug Substances and Products, November 1996). This equates to 240,000 lux-hours of visible light and 40 watt-hour/m$^2$ near-UV light. A Bahnson ES2000 photochamber (Environmental Specialties, a Bahnson Group Company) equipped with catalog 04030-307-CW visible and 04030-308UV near-UV lamps is used. Samples are exposed to visible light at 8,000 lux intensity for 30 hours and 10 watt/m$^2$ near-UV light for 4 hours. All exposures are at 25° C. in type I borosilicate glass HPLC vials. Following exposure, the percent HMW polymer formation is determined by SEC and is shown in Table 5(g).

TABLE 5(g)

Photostability of Bispecific Antibody 1 at 50 mg/mL in C6NT formulation

| % HMW increase (240,000 lux-hr visible) | % HMW increase (240,000 lux-hr visible plus 40 watt-hr/m$^2$ near-UV) |
|---|---|
| 3.4% | 5.9% |

Inhibition of IL-23-Mediated Stat 3 Activity In Vitro in Kit225 Cells

Kit225 is a human T-cell line established from a patient with T-cell chronic lymphocytic leukemia. These cells naturally express IL-23R/IL12Rβ1 and their response to human IL-23 results in phosphorylation and activation of the Stat-3 pathway. The ability of human IL-23 to activate the Stat-3 pathway is assessed by measuring luciferase activity in Kit225 cells stably transfected with Stat3-luciferase construct.

Kit225-Stat-3-luc (clone 3) cells are routinely cultured in assay medium. On the day of assay, cells are collected by centrifugation, washed with large volume of serum free medium and resuspended in serum free OPTI-MEM medium. Kit225 (50,000) cells are added to the wells of a white/clear bottom TC treated 96 well plate and treated with the agent of interest (Bispecific Antibody 1) in the presence of human IL-23. A dose range of Bispecific Antibody 1 from 0 to 208950 pM is evaluated. Human IL-23 is added to each well to a final concentration of 50 pM. The assay medium alone is used for "medium alone" and "hIL-23 alone" control.

An IL-23 neutralizing antibody (tested in a dose range from 0 to 100000 pM) is used as a positive control in the assay. An isotype control antibody tested in a dose range from 0 to 126790 pM is used as a negative control. Testing is carried out in triplicates. The plates are placed in tissue culture incubator for 4 hours and Bright-Glo Luciferase solution (Promega) is added to stop the assay upon the treatment. A Luminometer (Perkin Elmer Victor3) is used to read the plates. Results are expressed as the concentration where 50% of the IL-23-induced Stat-3 activity is inhibited (IC$_{50}$) by either Bispecific Antibody 1 or the positive control antibody and is calculated using a 4 parameter sigmoidal fit of the data (Sigma plot). In some experiments, 50 nM of human CGRP is added to the wells.

The results demonstrate that Bispecific Antibody 1 inhibits human IL-23 induced Stat 3 activity in Kit225 cells in a concentration-dependent manner. As Bispecific Antibody 1 has only one binding site that binds to human IL-23, the observed inhibition is lower than that seen with the positive control antibody, which has two binding sites for human IL-23 with an IC$_{50}$ of 1856.5±384.5 pM for Bispecific Antibody 1, versus 466±31 pM for the Positive Control antibody. The negative isotype control antibody does not inhibit Stat-3 activity in Kit225 cells at any concentration tested.

The addition of 50 nM of human CGRP to the assay did not modify the activity of Bispecific Antibody 1, since the IC$_{50}$ in presence of human CGRP (1193 pM) is comparable to that described above. The negative isotype control antibody does not inhibit Stat-3 activity in Kit225 cells at any concentration tested.

Bispecific Antibody 1 effectively neutralizes human IL-23 function in vitro and IL-23 inhibition is not affected by presence of human CGRP.

Inhibition of cAMP Production Induced by CGRP in SK-N-MC Cells In Vitro

SK-N-MC cells are a human neuroblastoma cell line that endogenously expresses the CGRP receptor. This receptor is functionally coupled to intracellular Gαs proteins. Stimulation of the receptor with its natural agonist, human CGRP peptide, results in an increased synthesis of cAMP. As the amount of cAMP present within cells can be detected using standard in vitro technology, this parameter is used as a measure of receptor activity.

Cultured SK-N-MC are grown in MEM supplemented with 10% heat-inactivated FBS, Non-Essential Amino Acids, 1 mM sodium pyruvate, 2 mM L-glutamine, 100 U/mL of penicillin, and 10 ug/mL of streptomycin to about 70% confluency. After providing fresh medium, the cells are incubated at 37° C. overnight. On the day of the assay, cells are detached using Accutase, resuspended in assay buffer (HBSS/DPBS with Mg$^{++}$ and Ca$^{++}$ mixed 1:2, 3.3 mM HEPES, 0.03% BSA, 0.5 mM IBMX), and seeded 3-5K/well into 384-well, poly-D-lysine coated white plates.

Bispecific Antibody 1 is diluted 1:3 in assay buffer from 10 nM to 0.5 pM (MW of bispecific antibody is 150 kDa). Diluted Bispecific Antibody 1, positive control Antibody (a CGRP neutralizing antibody described in U.S. Patent Application Serial No. US 2011/305711 A), or an isotype control antibody are mixed with or without human IL-23 (10 nM, final concentration) or an equal volume of buffer and incubated with the cells for 30 minutes at room temperature. Human CGRP peptide (Bachem H-1470) is added at its $EC_{80}$ concentration (0.8 nM), and the plates are incubated for 60 minutes at room temperature.

The signal window is established using 10 nM BIBN 4096 (olcegepant) (Tocris), a potent small molecule reference antagonist (Kb=0.01 nM). The amount of intracellular cAMP is quantitated using HTRF technology (Homogeneous Time Resolved Fluorescence; Cisbio) as per vendor instructions. Briefly, cAMP-d2 conjugate and anti-cAMP-cryptate conjugate in lysis buffer are incubated with the treated cells at room temperature for 60-90 minutes. The HTRF signal is immediately detected using an EnVision plate reader (Perkin-Elmer) to calculate the ratio of fluorescence at 665 to 620 nM. The raw data are converted to cAMP amount (pmole/well) using a cAMP standard curve generated for each experiment. Relative $EC_{50}$ values are calculated from the top-bottom range of the concentration response curve using a four-parameter logistic curve fitting program (ActivityBase v5.3.1.22 or Genedata Screener v12.0.4), and Kb values are estimated as agonist-corrected $IC_{50}$ values using the equation: $Kb=(IC_{50})/[1+([Ag]/EC_{50})]$.

The results demonstrate that Bispecific Antibody 1 inhibits CGRP-stimulated cAMP production in a dose-dependent manner, with an estimated Kb of 0.04 nM and a maximum effect equal to that produced by a Positive Control Antibody (Table 6). The presence of 10 nM human IL-23 has no effect on the inhibition by Bispecific Antibody 1 or the positive control. In contrast, the isotype control antibody does not inhibit CGRP-induced cAMP production at any concentration tested.

TABLE 6

Inhibition of CGRP-induced cAMP production by test antibodies.

| Antibody | Kb (nM) + SEM | | Maximum % Activity + SEM | |
| --- | --- | --- | --- | --- |
| | −IL-23 | +IL-23 | −IL-23 | +IL-23 |
| Bispecific Antibody 1 | 0.04 ± 0.008 | 0.04 ± 0.002 | 99.8 ± 0.05 | 99.7 ± 0.06 |
| Isotype Control | >2.5 | >2.5 | 3.3 ± 0.42 | 6.9 ± 2.0 |
| Positive Control | 0.02 ± 0.003 | 0.03 ± 0.006 | 99.9 ± 0.03 | 99.8 ± 0 |

Inhibition of Human IL-23-Induced Mouse IL-22 Production In Vivo

Administration of human IL-23 induces production of mouse IL-22 in normal Balb/c mice in vivo. To understand if Bispecific Antibody 1 will block human IL-23-induced production of mouse IL-22, in vivo Balb/c mice (n=5) are injected IP with 0.312, 1.25 or 5 mg/kg of Bispecific Antibody 1 or with 2.5 mg/kg of anti-IL-23 antibody (Positive Control) or with 5 mg/kg of an Isotype Control antibody. Two days post-injection, mice are challenged by IP injection of 50 nmol/kg of human IL-23. Five hours post-human IL-23 challenge, mice are sacrificed and serum is collected. Serum is analyzed for mouse IL-22 production using a commercial ELISA and for exposure of antibodies.

The results demonstrate that treatment with Bispecific Antibody 1 neutralizes human IL-23 function in a concentration-dependent manner and produces statistically significant inhibition compared to isotype control at all doses. The results observed with Bispecific Antibody 1 are comparable to the Positive Control antibody's inhibition. The negative control antibody does not inhibit the human IL-23-induced increase in production of mouse IL-22.

This study demonstrates that Bispecific Antibody 1 inhibits production of mouse IL-22 through neutralization of human IL-23 function in vivo.

Inhibition of Capsaicin-Induced Increase in Rat Dermal Blood Flow

The capsaicin induced Laser Doppler Imaging (LDI) blood flow method is based on a capsaicin solution topically applied to the skin, which induces a local change in dermal blood flow (DBF) that can be monitored using LDI. This method is dependent on capsaicin activation of the Transient Receptor Potential cation channel subfamily V member 1 (TRPV1) receptor followed by a local release of CGRP and activation of the CGRP receptor on the blood vessels in the skin. The capsaicin-induced dermal vasodilation model is applied to assess target engagement in pre-clinical models and is translational to the clinic.

Bispecific Antibody 1, Positive Control (an anti-CGRP neutralizing antibody described in U.S. Patent Application Serial No. US 2011/305711 A) and Isotype Control (human IgG1) are prepared in PBS. Lewis Rats (n=8 per group) are treated with Bispecific Antibody 1 SC at 8, 4 and 1 mg/kg, Positive Control or Isotype Control SC at 4 mg/kg 5 days prior to the LDI measurement and fasted overnight prior to the experiment. Study operators are blinded to the treatments.

On the day of LDI measurement, the rats are anesthetized with isoflurane and their abdomens are shaved prior to scanning. The rats are placed on a warm heating pad, under laser head and the animal's body temperature is stabilized while under ~1% isoflurane anesthesia for ~15 minutes prior to scanning. During this stabilization period, preliminary scans are obtained for correct positioning of the three neoprene O-rings (away from visible blood vessels and high basal blood flow areas). The scan series begins with two baseline scans. After scan two is completed, 8 µL (2 mg) of capsaicin solution is applied to each of the three O-rings (100 mg of capsaicin in a solution of 120 µL ETOH, 80 µL Tween 20, 200 µL purified H2O). Scanning continues with a scan every 2.5 minutes for an additional 25 minutes. Once scans are completed, an IV blood sample is obtained for serum analysis. Raw data is analyzed with moorLDI version 5.3 software by selecting circular regions of interest (ROI) inside each of the O-rings. An average of the pixels in each ROI in perfusion units (PU) is obtained and used to calculate relative changes in blood flow for each scan. The mean of the first two scans in each series is used as a baseline, and subsequent scans are normalized with the baseline values using the formula ((scan PU−average baseline PU)/average baseline PU))×100=percent change in blood flow. Analyzed data is entered into Graphpad Prism 6 for graphing and ANOVA is used for statistical analysis. Areas under the curve (from 10 to 25 minutes) of LDI Flux following capsaicin administration are compared to determine the CGRP inhibitory effects of the tested antibodies.

Treatment with Bispecific Antibody 1 at 1, 4 and 8 mg/kg produces statistically significant inhibition vs Isotype Control IgG at all doses with capsaicin-induced DBF reductions of 84.8%±4.7, 88.5%±6.0 and 66.3%±10.0 respectively. Treatment with the positive control at 4 mg/kg produces a statistically significant 82.9%±5.6 inhibition. There are no statistically significant differences between any dose of Bispecific Antibody 1 and the anti-CGRP positive control antibody.

The results show that all doses of Bispecific Antibody 1 prevent CGRP-mediated capsaicin-induced DBF, whereas in contrast, control IgG1 does not, and the extent of the inhibition is equal to that achieved by the positive control antibody.

Nonclinical PK of Bispecific Antibody 1 in Monkey

Serum pharmacokinetics of Bispecific Antibody 1 is determined as follows: male cynomolgus monkeys are administered 5 mg/kg of Bispecific Antibody 1 either intravenously (IV) (N=1) or subcutaneously (SC) (N=2). Bispecific Antibody 1 is prepared in solution of PBS (pH 7.4).

Blood samples (approximately 1 mL) are collected pre-dose and at 1, 6, 12, 24, 48, 72, 96, 120, 144, 168, 240, 336, 504, and 672 hours post-dose. Blood samples are collected intravenously from a femoral vein into serum separator tubes (e.g., containing no anticoagulant) and processed to serum.

Serum samples are analyzed by quantitative LC/MS or antigen capture ELISA for total IgG. For antigen capture ELISA, the plates are coated with biotinylated CGRP (Bachem 4038212.0500). A mouse anti-human IgG-Fc horseradish peroxidase conjugate (SB 9040-05) is used to detect Bispecific Antibody 1. The antibody quantification range is 1.56-100 ng/mL in monkey serum. For quantitative LC/MS, samples are immunoprecipitated with biotinylated goat anti-hIgG (Southern Biotech, 2049-08) and streptavidin coated magnetic beads. Following immunoprecipitation samples are reduced, alkylated, and digested with trypsin. Total IgG concentrations are determined using selected tryptic peptides as a surrogate measure of antibody exposure. Detection and integration of data are performed using a Thermo Q-Exactive Orbitrap LC/MS system. The quantification range is 25-12,800 ng/mL in monkey serum.

Pharmacokinetic parameters (clearance values) are calculated using concentration versus time profile from time zero (administration of antibody) to 672 hour post administration and are determined via non-compartmental analysis using Phoenix (WinNonLin 6.4, Connect 1.4). Results are summarized in Table 7.

TABLE 7

Antibody clearance of Bispecific Antibody 1 in cynomolgus monkey following single IV or SC administration.

| Antibody Administered | IV Clearance (mL/hr/kg) | SC Clearance (mL/hr/kg) |
|---|---|---|
| Bispecific Antibody 1 | 0.307 | 0.365 |

SEQUENCES

Human CGRP amino acid sequence (SEQ ID NO: 1)
ACDTATCVTHRLAGLLSRSGGVVKNNFVPTNVGSKAF -continued

SEQUENCES

Mature p19 subunit of human IL-23 amino acid
sequence (SEQ ID NO: 2)
RAVPGGSSPAWTQCQQLSQKLCTLAWSAHPLVGHMDLREEGDEETTNDV
PHIQCGDGCDPQGLRDNSQFCLQRIHQGLIFYEKLLGSDIFTGEPSLLP
DSPVGQLHASLLGLSQLLQPEGHHWETQQIPSLSPSQPWQRLLLRFKIL
RSLQAFVAVAARVFAHGAATLSP First heavy chain variable region (anti-CGRP)
amino acid sequence (SEQ ID NO: 3)
QVQLVQSGAEVKKPGSSVKVSCKASGYTFGNYWMQWVRYAPGQGLEWMG
AIYEGTGKTVYIQKFADRVTITADKSTSTAYMELSSLRSEDTAVYYCAR
LSDYVSGFGYWGRGTTVTVSS First light chain variable region (anti-CGRP)
amino acid sequence (SEQ ID NO: 4)
DIQMTQSPSSLSASVGDRVTITCRASKDISKYLNWYQRKPGDAPKLLIY
YTSGYHSGVPSRFSGSGSGTDFTLTISSLQPEDFATYYCQQGDALPPTF
GGGTKVEIK Second heavy chain variable region (anti-IL-23)
amino acid sequence (SEQ ID NO: 5)
QVQLVQSGAEVKKPGSSVKVSCKASGYPFTRYVMHWVRKAPGQGLEWMG
YINPYNDGVNYNEEFKGRVTITADESTSTAYMELSSLRSEDTAVYYCAR
NWDTGLWGQGTTVTVSS Second light chain variable region (anti-IL-23)
amino acid sequence (SEQ ID NO: 6)
RIQMTQSPSSLSASVGDRVTITCKASDHIGKFLTWYQDKPGKAPKLLIY
GATSKLTGVPSRFSGSGSGTDFTLTISSLQPEDFATYYCQQYWSTPFTF
GGGTKVEIK First heavy chain (anti-CGRP) amino acid sequence
(SEQ ID NO: 7)
QVQLVQSGAEVKKPGSSVKVSCKASGYTFGNYWMQWVRYAPGQGLEWMG
AIYEGTGKTVYIQKFADRVTITADKSTSTAYMELSSLRSEDTAVYYCAR
LSDYVSGFGYWGRGTTVTVSSASTKGPSVFPLAPCSKSTSGGTAALGCL
VKDYFPEPVTVSWNSGALTSGVHTFPAVLQSSGLYSLSSVVTVPSSSLG
TQTYICNVNHKPSNTKVDKKVEPDSGDKTHTCPPCPAPEAAGGPSVFLF
PPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKG
QPREPQVYTLPPSRGDMTKNQVQLTCLVKGFYPSDIAVEWESNGQPENN
YKTTPPVLDSDGSFFLASKLTVDKSRWQQGNVFSCSVMHEALHNHYTQK
SLSLSPG First light chain (anti-CGRP) amino acid sequence
(SEQ ID NO: 8)
DIQMTQSPSSLSASVGDRVTITCRASKDISKYLNWYQRKPGDAPKLLIY
YTSGYHSGVPSRFSGSGSGTDFTLTISSLQPEDFATYYCQQGDALPPTF
GGGTKVEIKRTVAAPSVFIFPPSKEQLKSGTASVVCLLNNFYPREAKVQ
WKVDNALQSGNSQESVTEQDSKDSTYSLSSTLTLSKADYEKHKVYACEV
THQGLSSPVTKSFNRGEC Second heavy chain (anti-IL-23) amino acid
sequence (SEQ ID NO: 9)
QVQLVQSGAEVKKPGSSVKVSCKASGYPFTRYVMHWVRKAPGQGLEWMG
YINPYNDGVNYNEEFKGRVTITADESTSTAYMELSSLRSEDTAVYYCAR
NWDTGLWGQGTTVTVSSASTKGPSVFPLAPSSKSTSGGTAALGCLVKDY
FPEPVTVSWNSGALTSGVATGPAVLQSSGLYSLSSVVTVPSSSLGTQTY
ICNVNHKPSNTKVDKKVEPKSCDKTHTCPPCPAPEAAGGPSVFLFPPKP
KDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPRE
PQVSTLPPSREEMTKNQVSLMCLVYGFYPSDIAVEWESNGQPENNYKTT
PPVLDSDGSFFLYSVLTVDKSRWQQGNVF SCSVMHEALHNHYTQKSLS
LSPG Second light chain (anti-IL-23) amino acid
sequence (SEQ ID NO: 10)
RIQMTQSPSSLSASVGDRVTITCKASDHIGKFLTWYQDKPGKAPKLLIY
GATSKLTGVPSRFSGSGSGTDFTLTISSLQPEDFATYYCQQYWSTPFTF
GGGTKVEIKGQPKAAPSVTLFPPSSEELQANKATLVCYISDFYPGAVTV
AWKADSSPVKAGVETTTPSKQSNNKYAAWSYLSLTPEQWKSHRSYSCQV
THEGSTVEKTVAPTEC First heavy chain (anti-CGRP) CDR amino acid
sequences
H1CDR-1 (SEQ ID NO: 12)

KASGYTFGNWMQ

H1CDR-2 (SEQ ID NO: 14)
AIYEGTGKTVYIQKFAD

H1CDR-3 (SEQ ID NO: 16)
ARLSDYVSGFGY

First heavy chain (anti-CGRP) FR amino acid
sequences
H1FR-1 (SEQ ID NO: 11)
QVQLVQSGAEVKKPGSSVKVSC

H1FR-2 (SEQ ID NO: 13)
WVRYAPGQGLEWMG

H1FR-3 (SEQ ID NO: 15)
RVTITADKSTSTAYMELSSLRSEDTAVYYC

H1FR-4 (SEQ ID NO: 17)
WGRGTTVTVSS

First heavy chain (anti-CGRP) constant region
(HC1CR) amino acid sequence (SEQ ID NO: 18)
ASTKGPSVFPLAPCSKSTSGGTAALGCLVKDYFPEPVTVSWNSGALTSG
VHTFPAVLQSSGLYSLSSVVTVPSSSLGTQTYICNVNHKPSNTKVDKKV
EPDSGDKTHTCPPCPAPEAAGGPSVFLFPPKPKDTLMISRTPEVTCVVV
DVSHEDPEVKFNWYVDGVEVHNAKTKPREEQYNSTYRVVSVLTVLHQDW
LNGKEYKCKVSNKALPAPIEKTISKAKGQPREPQVYTLPPSRGDMTKNQ
VQLTCLVKGFYPSDIAVEWESNGQPENNYKTTPPVLDSDGSFFLASKLT
VDKSRWQQGNVFSCSVMHEALHNHYTQKSLSLSPG First heavy chain (anti-CGRP) $C_H1$ (H1$C_H$1) amino
acid sequence (SEQ ID NO: 19)
ASTKGPSVFPLAPCSKSTSGGTAALGCLVKDYFPEPVTVSWNSGALTSG
VHTFPAVLQSSGLYSLSSVVTVPSSSLGTQTYICNVNHKPSNTKVDKKV First heavy chain (anti-CGRP) hinge region amino
acid sequence (SEQ ID NO: 49)
EPDSGDKTHTCPPCP First heavy chain (anti-CGRP) $C_H2$ (H1$C_H$2) amino
acid sequence (SEQ ID NO: 20)
APEAAGGPSVFLFPPKPKDTLMISRTPEVTCVVVDVSHEDPEVKFNWYV
DGVEVHNAKTKPREEQYNSTYRVVSVLTVLHQDWLNGKEYKCKVSNKAL
PAPIEKTISKAK First heavy chain (anti-CGRP) $C_H3$ (H1$C_H$3) amino
acid sequence (SEQ ID NO: 21)
GQPREPQVYTLPPSRGDMTKNQVQLTCLVKGFYPSDIAVEWESNGQPEN
NYKTTPPVLDSDGSFFLASKLTVDKSRWQQGNVFSCSVMHEALHNHYTQ
KSLSLSPG Second heavy chain (anti-IL-23) CDR amino acid
sequences
H2CDR-1 (SEQ ID NO: 23)
KASGYPFTRYVMH

H2CDR-2 (SEQ ID NO: 25)
YINPYNDGVNYNEEFKG

H2CDR-3 (SEQ ID NO: 27)
ARNWDTGL

Second heavy chain (anti-IL-23) FR amino acid
sequences
H2FR-1 (SEQ ID NO: 22)
QVQLVQSGAEVKKPGSSVKVSC

H2FR-2 (SEQ ID NO: 24)
WVRKAPGQGLEWMG

H2FR-3 (SEQ ID NO: 26)
RVTITADESTSTAYMELSSLRSEDTAVYYC

H2FR-4 (SEQ ID NO: 28)
WGQGTTVTVSS

Second heavy chain (anti-IL-23) constant region
(HC2CR) amino acid sequence (SEQ ID NO: 29)
ASTKGPSVFPLAPSSKSTSGGTAALGCLVKDYFPEPVTVSWNSGALTSG
VATGPAVLQSSGLYSLSSVVTVPSSSLGTQTYICNVNHKPSNTKVDKKV
EPKSCDKTHTCPPCPAPEAAGGPSVFLFPPKPKDTLMISRTPEVTCVVV
DVSHEDPEVKFNWYVDGVEVHNAKTKPREEQYNSTYRVVSVLTVLHQDW
LNGKEYKCKVSNKALPAPIEKTISKAKGQPREPQVSTLPPSREEMTKNQ
VSLMCLVYGFYPSDIAVEWESNGQPENNYKTTPPVLDSDGSFFLYSVLT
VDKSRWQQGNVFSCSVMHEALHNHYTQKSLSLSPG Second heavy chain (anti-IL-23) $C_H1$ (H2$C_H$1) amino
acid sequence (SEQ ID NO: 30)
ASTKGPSVFPLAPSSKSTSGGTAALGCLVKDYFPEPVTVSWNSGALTSG
VATGPAVLQSSGLYSLSSVVTVPSSSLGTQTYICNVNHKPSNTKVDKKV Second heavy chain (anti-IL-23) hinge region
amino acid sequence (SEQ ID NO: 50)
EPKSCDKTHTCPPCP Second heavy chain (anti-IL-23) $C_H2$ (H2$C_H$2) amino
acid sequence (SEQ ID NO: 31)
APEAAGGPSVFLFPPKPKDTLMISRTPEVTCVVVDVSHEDPEVKFNWYV
DGVEVHNAKTKPREEQYNSTYRVVSVLTVLHQDWLNGKEYKCKVSNKAL
PAPIEKTISKAK Second heavy chain (anti-IL-23) $C_H3$ (H2$C_H$3) amino
acid sequence (SEQ ID NO: 32)
GQPREPQVSTLPPSREEMTKNQVSLMCLVYGFYPSDIAVEWESNGQPEN
NYKTTPPVLDSDGSFFLYSVLTVDKSRWQQGNVFSCSVMHEALHNHYTQ
KSLSLSPG First light chain (anti-CGRP) CDR amino acid
sequences
L1CDR-1 (SEQ ID NO: 34)
RASKDISKYLN

L1CDR-2 (SEQ ID NO: 36)
YYTSGYHS

L1CDR-3 (SEQ ID NO: 38)
QQGDALPPT

First light chain (anti-CGRP) FR amino acid
sequences
L1FR-1 (SEQ ID NO: 33)
DIQMTQSPSSLSASVGDRVTITC

L1FR-2 (SEQ ID NO: 35)
WYQRKPGDAPKLLI

L1FR-3 (SEQ ID NO: 37)
GVPSRFSGSGSGTDFTLTISSLQPEDFATYYC

L1FR-4 (SEQ ID NO: 39)
FGGGTKVEIK

First light chain (anti-CGRP) constant region
(LC1CR) amino acid sequence (SEQ ID NO: 40)
RTVAAPSVFIFPPSKEQLKSGTASVVCLLNNFYPREAKVQWKVDNALQS
GNSQESVTEQDSKDSTYSLSSTLTLSKADYEKHKVYACEVTHQGLSSPV
TKSFNRGEC Second light chain (anti-IL-23) CDR amino acid
sequences
L2CDR-1 (SEQ ID NO: 42)
KASDHIGKFLT

L2CDR-2 (SEQ ID NO: 44)
YGATSKLT

L2CDR-3 (SEQ ID NO: 46)
QQYWSTPFT

Second light chain (anti-IL23) FR amino acid
sequences
L2FR-1 (SEQ ID NO: 41)

| SEQUENCES |
|---|
| RIQMTQSPSSLSASVGDRVTITC |
| L2FR-2 (SEQ ID NO: 43)<br>WYQDKPGKAPKLLI |
| L2FR-3 (SEQ ID NO: 45)<br>GVPSRFSGSGSGTDFTLTISSLQPEDFATYYC |
| L2FR-4 (SEQ ID NO: 47) |

| SEQUENCES |
|---|
| FGGGTKVEIK |
| Second light chain (anti-IL23) constant region (LC2CR) amino acid sequence (SEQ ID NO: 48)<br>GQPKAAPSVTLFPPSSEELQANKATLVCYISDFYPGAVTVAWKADSSPV<br>KAGVETTTPSKQSNNKYAAWSYLSLTPEQWKSHRSYSCQVTHEGSTVEK<br>TVAPTEC |

We claim:

1. An IgG bispecific antibody comprising:
   a) a first heavy chain (HC1) comprising a first heavy chain variable region (HC1VR) having the amino acid sequence of SEQ ID NO: 3;
   b) a first light chain (LC1) comprising a first light chain variable region (LC1VR) having the amino acid sequence of SEQ ID NO: 4;
   c) a second heavy chain (HC2) comprising a second heavy chain variable region (HC2VR) having the amino acid sequence of SEQ ID NO: 5; and
   d) a second light chain (LC2) comprising a second light chain variable region (LC2VR) having the amino acid sequence of SEQ ID NO: 6,
   wherein HC1 forms at least one inter-chain disulfide bond with LC1, HC2 forms at least one inter-chain disulfide bond with LC2, and HC1 forms at least one inter-chain disulfide bond with HC2, and wherein the antibody binds to human calcitonin gene related peptide (CGRP) and the p19 subunit of human IL-23.

2. The IgG bispecific antibody according to claim 1, wherein HC1 and HC2 are human IgG$_1$ HCs, LC1 is a human kappa light chain and LC2 is a human lambda light chain, and wherein
   i) HC1 has a cysteine residue at position 127 (Kabat) of the HC1 C$_H$1 domain (HC1C$_H$1), an aspartic acid residue at position 228 (Kabat) of the HC1 hinge domain, a glycine residue at position 222 (Kabat) of the HC1 hinge domain, a glycine residue at position 356 (EU) of the HC1 C$_H$3 domain, an aspartic acid residue at position 357 (EU) of the HC1 C$_H$3 domain, a glutamine residue at position 364 (EU) of the HC1 C$_H$3 domain, and an alanine residue at position 407 (EU) of the HC1 C$_H$3 domain;
   ii) HC2 has an alanine residue at position 166 (Kabat) of the HC2 C$_H$1 domain, a glycine residue at position 170 (Kabat) of the HC2 C$_H$1 domain, a serine residue at position 349 (EU) of the HC2 C$_H$3 domain, a methionine residue at position 366 (EU) of the HC2 C$_H$3 domain, a tyrosine residue at position 370 (EU) of the HC2 C$_H$3 domain, and a valine residue at position 409 (EU) of the HC2 C$_H$3 domain;
   iii) LC1 has a lysine residue at position 122 (Kabat) of the LC1 C$_L$ domain; and
   iv) LC2 has a tyrosine residue at position 135 (Kabat) of the LC2 C$_L$ domain, and a tryptophan residue at position 176 (Kabat) of the LC2 C$_L$ domain.

3. The IgG bispecific antibody according to claim 2, wherein HC1 has an alanine residue at position 234 (Kabat) of the HC1 C$_H$2 domain and an alanine residue at position 235 (Kabat) of the HC1 C$_H$2 domain, and HC2 has an alanine residue at position 234 (Kabat) of the HC2 C$_H$2 domain and an alanine residue at position 235 (Kabat) of the HC2 C$_H$2 domain.

4. The IgG bispecific antibody according to claim 1, wherein HC1 and HC2 are human IgG$_4$ HCs, LC1 is a human kappa light chain and LC2 is a human lambda light chain, and wherein
- i) HC1 has a cysteine residue at position 127 (Kabat) of the HC1 C$_H$1 domain (HC1C$_H$1), an aspartic acid residue at position 228 (Kabat) of the HC1 hinge domain, a glycine residue at position 222 (Kabat) of the HC1 hinge domain, a glycine residue at position 356 (EU) of the HC1 C$_H$3 domain, an aspartic acid residue at position 357 (EU) of the HC1 C$_H$3 domain, a glutamine residue at position 364 (EU) of the HC1 C$_H$3 domain, and an alanine residue at position 407 (EU) of the HC1 C$_H$3 domain;
- ii) HC2 has an alanine residue at position 166 (Kabat) of the HC2 C$_H$1 domain, a glycine residue at position 170 (Kabat) of the HC2 C$_H$1 domain, a serine residue at position 349 (EU) of the HC2 C$_H$3 domain, a methionine residue at position 366 (EU) of the HC2 C$_H$3 domain, a tyrosine residue at position 370 (EU) of the HC2 C$_H$3 domain, and a valine residue at position 409 (EU) of the HC2 C$_H$3 domain;
- iii) LC1 has a lysine residue at position 122 (Kabat) of the LC1 C$_L$ domain; and
- iv) LC2 has a tyrosine residue at position 135 (Kabat) of the LC2 C$_L$ domain, and a tryptophan residue at position 176 (Kabat) of the LC2 C$_L$ domain.

5. The IgG bispecific antibody according to claim 1, wherein the bispecific antibody comprises:
- a) a first HC (HC1) having the amino acid sequence of SEQ ID NO: 7;
- b) a first LC (LC1) having the amino acid sequence of SEQ ID NO: 8;
- c) a second HC (HC2) having the amino acid sequence of SEQ ID NO: 9; and
- d) a second LC (LC2) having the amino acid sequence of SEQ ID NO: 10, wherein HC1 forms an inter-chain disulfide bond with LC1, HC2 forms an inter-chain disulfide bond with LC2, and HC1 forms at least one inter-chain disulfide bond with HC2, and wherein the antibody binds to human calcitonin gene related peptide (CGRP) and the p19 subunit of human IL-23.

6. A pharmaceutical composition comprising the IgG bispecific antibody according to claim 1, and an acceptable carrier, diluent, or excipient.

7. The pharmaceutical composition of claim 6, wherein the IgG bispecific antibody comprises:
- a) a first HC (HC1) having the amino acid sequence of SEQ ID NO: 7;
- b) a first LC (LC1) having the amino acid sequence of SEQ ID NO: 8;
- c) a second HC (HC2) having the amino acid sequence of SEQ ID NO: 9; and
- d) a second LC (LC2) having the amino acid sequence of SEQ ID NO: 10, wherein HC1 forms an inter-chain disulfide bond with LC1, HC2 forms an inter-chain disulfide bond with LC2, and HC1 forms at least one inter-chain disulfide bond with HC2, and wherein the antibody binds to human calcitonin gene related peptide (CGRP) and the p19 subunit of human IL-23.

8. A method of treating one of inflammatory bowel disease (IBD), psoriasis, palmoplantar pustulosis, psoriatic arthritis (PsA), ankylosing spondylitis (AS) and atopic dermatitis (AtD) comprising administering to a patient in need thereof an effective amount of the IgG bispecific antibody according to claim 1.

9. The method according to claim 8, wherein the IBD is Crohn's Disease (CD) or ulcerative colitis (UC).

10. The method of claim 9, wherein the IgG bispecific antibody comprises:
- a) a first HC (HC1) having the amino acid sequence of SEQ ID NO: 7;
- b) a first LC (LC1) having the amino acid sequence of SEQ ID NO: 8;
- c) a second HC (HC2) having the amino acid sequence of SEQ ID NO: 9; and
- d) a second LC (LC2) having the amino acid sequence of SEQ ID NO: 10, wherein HC1 forms an inter-chain disulfide bond with LC1, HC2 forms an inter-chain disulfide bond with LC2, and HC1 forms at least one inter-chain disulfide bond with HC2, and wherein the antibody binds to human calcitonin gene related peptide (CGRP) and the p19 subunit of human IL-23.

11. The method of claim 8, wherein the IgG bispecific antibody comprises:
- a) a first HC (HC1) having the amino acid sequence of SEQ ID NO: 7;
- b) a first LC (LC1) having the amino acid sequence of SEQ ID NO: 8;
- c) a second HC (HC2) having the amino acid sequence of SEQ ID NO: 9; and
- d) a second LC (LC2) having the amino acid sequence of SEQ ID NO: 10, wherein HC1 forms an inter-chain disulfide bond with LC1, HC2 forms an inter-chain disulfide bond with LC2, and HC1 forms at least one inter-chain disulfide bond with HC2, and wherein the antibody binds to human calcitonin gene related peptide (CGRP) and the p19 subunit of human IL-23.

12. A method of treating pain associated with one of inflammatory bowel disease (IBD), psoriasis, palmoplantar pustulosis, psoriatic arthritis (PsA), ankylosing spondylitis (AS) and atopic dermatitis (AtD) comprising administering to a patient in need thereof of an effective amount of the IgG bispecific antibody according to claim 1.

13. The method of treating pain according to claim 12, wherein the IBD is Crohn's Disease (CD) and the pain is associated with CD or wherein the IBD is ulcerative colitis (UC) and the pain is associated with UC.

14. The method of claim 13, wherein the IgG bispecific antibody comprises
- a) a first HC (HC1) having the amino acid sequence of SEQ ID NO: 7;
- b) a first LC (LC1) having the amino acid sequence of SEQ ID NO: 8;
- c) a second HC (HC2) having the amino acid sequence of SEQ ID NO: 9; and
- d) a second LC (LC2) having the amino acid sequence of SEQ ID NO: 10, wherein HC1 forms an inter-chain disulfide bond with LC1, HC2 forms an inter-chain disulfide bond with LC2, and HC1 forms at least one inter-chain disulfide bond with HC2, and wherein the antibody binds to human calcitonin gene related peptide (CGRP) and the p19 subunit of human IL-23.

15. The method of claim 12, wherein the IgG bispecific antibody comprises
- a) a first HC (HC1) having the amino acid sequence of SEQ ID NO: 7;
- b) a first LC (LC1) having the amino acid sequence of SEQ ID NO: 8;
- c) a second HC (HC2) having the amino acid sequence of SEQ ID NO: 9; and
- d) a second LC (LC2) having the amino acid sequence of SEQ ID NO: 10, wherein HC1 forms an inter-chain disulfide bond with LC1, HC2 forms an inter-chain disulfide bond with LC2, and HC1 forms at least one inter-chain disulfide bond with HC2, and wherein the antibody binds to human calcitonin gene related peptide (CGRP) and the p19 subunit of human IL-23.

* * * * *

SEQUENCE LISTING

<160> NUMBER OF SEQ ID NOS: 50

<210> SEQ ID NO 1
<211> LENGTH: 37
<212> TYPE: PRT
<213> ORGANISM: Homo sapiens

<400> SEQUENCE: 1

Ala Cys Asp Thr Ala Thr Cys Val Thr His Arg Leu Ala Gly Leu Leu
1               5                   10                  15

Ser Arg Ser Gly Gly Val Val Lys Asn Asn Phe Val Pro Thr Asn Val
            20                  25                  30

Gly Ser Lys Ala Phe
        35

<210> SEQ ID NO 2
<211> LENGTH: 170
<212> TYPE: PRT
<213> ORGANISM: Homo sapiens

<400> SEQUENCE: 2

Arg Ala Val Pro Gly Gly Ser Ser Pro Ala Trp Thr Gln Cys Gln Gln
1               5                   10                  15

Leu Ser Gln Lys Leu Cys Thr Leu Ala Trp Ser Ala His Pro Leu Val
            20                  25                  30

Gly His Met Asp Leu Arg Glu Glu Gly Asp Glu Glu Thr Thr Asn Asp
        35                  40                  45

Val Pro His Ile Gln Cys Gly Asp Gly Cys Asp Pro Gln Gly Leu Arg
    50                  55                  60

Asp Asn Ser Gln Phe Cys Leu Gln Arg Ile His Gln Gly Leu Ile Phe
65                  70                  75                  80

Tyr Glu Lys Leu Leu Gly Ser Asp Ile Phe Thr Gly Glu Pro Ser Leu
                85                  90                  95

Leu Pro Asp Ser Pro Val Gly Gln Leu His Ala Ser Leu Leu Gly Leu
            100                 105                 110

Ser Gln Leu Leu Gln Pro Glu Gly His His Trp Glu Thr Gln Gln Ile
        115                 120                 125

Pro Ser Leu Ser Pro Ser Gln Pro Trp Gln Arg Leu Leu Leu Arg Phe
    130                 135                 140

Lys Ile Leu Arg Ser Leu Gln Ala Phe Val Ala Val Ala Ala Arg Val
145                 150                 155                 160

Phe Ala His Gly Ala Ala Thr Leu Ser Pro
                165                 170

<210> SEQ ID NO 3
<211> LENGTH: 119

```
<212> TYPE: PRT
<213> ORGANISM: Artificial Sequence
<220> FEATURE:
<223> OTHER INFORMATION: Synthetic Construct

<400> SEQUENCE: 3

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Gly Asn Tyr
            20                  25                  30

Trp Met Gln Trp Val Arg Tyr Ala Pro Gly Gln Gly Leu Glu Trp Met
        35                  40                  45

Gly Ala Ile Tyr Glu Gly Thr Gly Lys Thr Val Tyr Ile Gln Lys Phe
    50                  55                  60

Ala Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ser Asp Tyr Val Ser Gly Phe Gly Tyr Trp Gly Arg Gly
            100                 105                 110

Thr Thr Val Thr Val Ser Ser
            115

<210> SEQ ID NO 4
<211> LENGTH: 107
<212> TYPE: PRT
<213> ORGANISM: Artificial Sequence
<220> FEATURE:
<223> OTHER INFORMATION: Synthetic Construct

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Asp Ile Ser Lys Tyr
            20                  25                  30

Leu Asn Trp Tyr Gln Arg Lys Pro Gly Asp Ala Pro Lys Leu Leu Ile
        35                  40                  45

Tyr Tyr Thr Ser Gly Tyr His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asp Ala Leu Pro Pro
                85                  90                  95

Thr Phe Gly Gly Gly Thr Lys Val Glu Ile Lys
            100                 105

<210> SEQ ID NO 5
<211> LENGTH: 115
<212> TYPE: PRT
<213> ORGANISM: Artificial Sequence
<220> FEATURE:
<223> OTHER INFORMATION: Synthetic Construct

<400> SEQUENCE: 5

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Pro Phe Thr Arg Tyr
            20                  25                  30

Val Met His Trp Val Arg Lys Ala Pro Gly Gln Gly Leu Glu Trp Met
```

```
                35                  40                  45
Gly Tyr Ile Asn Pro Tyr Asn Asp Gly Val Asn Tyr Asn Glu Glu Phe
        50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Asp Thr Gly Leu Trp Gly Gln Gly Thr Thr Val Thr
            100                 105                 110

Val Ser Ser
        115

<210> SEQ ID NO 6
<211> LENGTH: 107
<212> TYPE: PRT
<213> ORGANISM: Artificial Sequence
<220> FEATURE:
<223> OTHER INFORMATION: Synthetic Construct

<400> SEQUENCE: 6

Arg Ile Gln Met Thr Gln Ser Pro Ser Ser Leu Ser Ala Ser Val Gly
1               5                   10                  15

Asp Arg Val Thr Ile Thr Cys Lys Ala Ser Asp His Ile Gly Lys Phe
            20                  25                  30

Leu Thr Trp Tyr Gln Asp Lys Pro Gly Lys Ala Pro Lys Leu Leu Ile
        35                  40                  45

Tyr Gly Ala Thr Ser Lys Leu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Trp Ser Thr Pro Phe
                85                  90                  95

Thr Phe Gly Gly Gly Thr Lys Val Glu Ile Lys
            100                 105

<210> SEQ ID NO 7
<211> LENGTH: 448
<212> TYPE: PRT
<213> ORGANISM: Artificial Sequence
<220> FEATURE:
<223> OTHER INFORMATION: Synthetic Construct

<400> SEQUENCE: 7

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Gly Asn Tyr
            20                  25                  30

Trp Met Gln Trp Val Arg Tyr Ala Pro Gly Gln Gly Leu Glu Trp Met
        35                  40                  45

Gly Ala Ile Tyr Glu Gly Thr Gly Lys Thr Val Tyr Ile Gln Lys Phe
    50                  55                  60

Ala Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ser Asp Tyr Val Ser Gly Phe Gly Tyr Trp Gly Arg Gly
            100                 105                 110
```

```
Thr Thr Val Thr Val Ser Ser Ala Ser Thr Lys Gly Pro Ser Val Phe
            115                 120                 125

Pro Leu Ala Pro Cys Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Asp Ser Gly Asp Lys
210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Gly Asp Met Thr Lys Asn Gln Val Gln Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Ala Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

<210> SEQ ID NO 8
<211> LENGTH: 214
<212> TYPE: PRT
<213> ORGANISM: Artificial Sequence
<220> FEATURE:
<223> OTHER INFORMATION: Synthetic Construct

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Asp Ile Ser Lys Tyr
            20                  25                  30
```

Leu Asn Trp Tyr Gln Arg Lys Pro Gly Asp Ala Pro Lys Leu Leu Ile
        35                  40                  45

Tyr Tyr Thr Ser Gly Tyr His Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Asp Ala Leu Pro Pro
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Lys Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 9
<211> LENGTH: 444
<212> TYPE: PRT
<213> ORGANISM: Artificial Sequence
<220> FEATURE:
<223> OTHER INFORMATION: Synthetic Construct

<400> SEQUENCE: 9

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Pro Phe Thr Arg Tyr
            20                  25                  30

Val Met His Trp Val Arg Lys Ala Pro Gly Gln Gly Leu Glu Trp Met
        35                  40                  45

Gly Tyr Ile Asn Pro Tyr Asn Asp Gly Val Asn Tyr Asn Glu Glu Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Asp Thr Gly Leu Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val Ala Thr Gly Pro Ala Val Leu Gln Ser Ser Gly
                165                 170                 175

Leu Tyr Ser Leu Ser Ser Val Val Thr Val Pro Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Ser Thr Leu Pro Pro Ser
            340                 345                 350

Arg Glu Glu Met Thr Lys Asn Gln Val Ser Leu Met Cys Leu Val Tyr
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Val Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 10
<211> LENGTH: 212
<212> TYPE: PRT
<213> ORGANISM: Artificial Sequence
<220> FEATURE:
<223> OTHER INFORMATION: Synthetic Construct

<400> SEQUENCE: 10

Arg Ile Gln Met Thr Gln Ser Pro Ser Ser Leu Ser Ala Ser Val Gly
1               5                   10                  15

Asp Arg Val Thr Ile Thr Cys Lys Ala Ser Asp His Ile Gly Lys Phe
            20                  25                  30

Leu Thr Trp Tyr Gln Asp Lys Pro Gly Lys Ala Pro Lys Leu Leu Ile
        35                  40                  45

Tyr Gly Ala Thr Ser Lys Leu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Trp Ser Thr Pro Phe
                85                  90                  95

Thr Phe Gly Gly Gly Thr Lys Val Glu Ile Lys Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Tyr Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Trp
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys
    210

<210> SEQ ID NO 11
<211> LENGTH: 22
<212> TYPE: PRT
<213> ORGANISM: Artificial Sequence
<220> FEATURE:
<223> OTHER INFORMATION: Synthetic Construct

<400> SEQUENCE: 11

Gln Val Gln Leu Val Gln Ser Gly Ala Glu Val Lys Lys Pro Gly Ser
1               5                   10                  15

Ser Val Lys Val Ser Cys
            20

<210> SEQ ID NO 12
<211> LENGTH: 13
<212> TYPE: PRT
<213> ORGANISM: Artificial Sequence
<220> FEATURE:
<223> OTHER INFORMATION: Synthetic Construct

<400> SEQUENCE: 12

Lys Ala Ser Gly Tyr Thr Phe Gly Asn Tyr Trp Met Gln
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Synthetic Construct

<400> SEQUENCE: 13

Trp Val Arg Tyr Ala Pro Gly Gln Gly Leu Glu Trp Met Gly
1               5                   10

<210> SEQ ID NO 14
<211> LENGTH: 17
<212> TYPE: PRT
<213> ORGANISM: Artificial Sequence
<220> FEATURE:
<223> OTHER INFORMATION: Synthetic Construct

<400> SEQUENCE: 14

Ala Ile Tyr Glu Gly Thr Gly Lys Thr Val Tyr Ile Gln Lys Phe Ala
1               5                   10                  15

Asp

<210> SEQ ID NO 15
<211> LENGTH: 30
<212> TYPE: PRT
<213> ORGANISM: Artificial Sequence
<220> FEATURE:
<223> OTHER INFORMATION: Synthetic Construct

<400> SEQUENCE: 15

Arg Val Thr Ile Thr Ala Asp Lys Ser Thr Ser Thr Ala Tyr Met Glu
1               5                   10                  15

Leu Ser Ser Leu Arg Ser Glu Asp Thr Ala Val Tyr Tyr Cys
            20                  25                  30

<210> SEQ ID NO 16
<211> LENGTH: 12
<212> TYPE: PRT
<213> ORGANISM: Artificial Sequence
<220> FEATURE:
<223> OTHER INFORMATION: Synthetic Construct

<400> SEQUENCE: 16

Ala Arg Leu Ser Asp Tyr Val Ser Gly Phe Gly Tyr
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Synthetic Construct

<400> SEQUENCE: 17

Trp Gly Arg Gly Thr Thr Val Thr Val Ser Ser
1               5                   10

<210> SEQ ID NO 18
<211> LENGTH: 329
<212> TYPE: PRT
<213> ORGANISM: Artificial Sequence
<220> FEATURE:
<223> OTHER INFORMATION: Synthetic Construct

<400> SEQUENCE: 18

Ala Ser Thr Lys Gly Pro Ser Val Phe Pro Leu Ala Pro Cys Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Asp Ser Gly Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys

```
            130                 135                 140
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Gly Asp
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Ala Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 19
<211> LENGTH: 98
<212> TYPE: PRT
<213> ORGANISM: Artificial Sequence
<220> FEATURE:
<223> OTHER INFORMATION: Synthetic Construct

<400> SEQUENCE: 19

Ala Ser Thr Lys Gly Pro Ser Val Phe Pro Leu Ala Pro Cys Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 20
<211> LENGTH: 110
<212> TYPE: PRT
<213> ORGANISM: Artificial Sequence
<220> FEATURE:
<223> OTHER INFORMATION: Synthetic Construct

<400> SEQUENCE: 20

Ala Pro Glu Ala Ala Gly Gly Pro Ser Val Phe Leu Phe Pro Pro Lys
```

```
                1               5                    10                   15
        Pro Lys Asp Thr Leu Met Ile Ser Arg Thr Pro Glu Val Thr Cys Val
                       20                  25                  30

Val Val Asp Val Ser His Glu Asp Pro Glu Val Lys Phe Asn Trp Tyr
                       35                  40                  45

Val Asp Gly Val Glu Val His Asn Ala Lys Thr Lys Pro Arg Glu Glu
         50                  55                  60

Gln Tyr Asn Ser Thr Tyr Arg Val Val Ser Val Leu Thr Val Leu His
         65                  70                  75                  80

Gln Asp Trp Leu Asn Gly Lys Glu Tyr Lys Cys Lys Val Ser Asn Lys
                            85                  90                  95

Ala Leu Pro Ala Pro Ile Glu Lys Thr Ile Ser Lys Ala Lys
                       100                 105                 110

<210> SEQ ID NO 21
<211> LENGTH: 106
<212> TYPE: PRT
<213> ORGANISM: Artificial Sequence
<220> FEATURE:
<223> OTHER INFORMATION: Synthetic Construct

<400> SEQUENCE: 21

Gly Gln Pro Arg Glu Pro Gln Val Tyr Thr Leu Pro Pro Ser Arg Gly
         1               5                   10                  15

Asp Met Thr Lys Asn Gln Val Gln Leu Thr Cys Leu Val Lys Gly Phe
                        20                  25                  30

Tyr Pro Ser Asp Ile Ala Val Glu Trp Glu Ser Asn Gly Gln Pro Glu
                    35                  40                  45

Asn Asn Tyr Lys Thr Thr Pro Pro Val Leu Asp Ser Asp Gly Ser Phe
         50                  55                  60

Phe Leu Ala Ser Lys Leu Thr Val Asp Lys Ser Arg Trp Gln Gln Gly
         65                  70                  75                  80

Asn Val Phe Ser Cys Ser Val Met His Glu Ala Leu His Asn His Tyr
                            85                  90                  95

Thr Gln Lys Ser Leu Ser Leu Ser Pro Gly
                    100                 105

<210> SEQ ID NO 22
<211> LENGTH: 22
<212> TYPE: PRT
<213> ORGANISM: Artificial Sequence
<220> FEATURE:
<223> OTHER INFORMATION: Synthetic Construct

<400> SEQUENCE: 22

Gln Val Gln Leu Val Gln Ser Gly Ala Glu Val Lys Lys Pro Gly Ser
         1               5                   10                  15

Ser Val Lys Val Ser Cys
                        20

<210> SEQ ID NO 23
<211> LENGTH: 13
<212> TYPE: PRT
<213> ORGANISM: Artificial Sequence
<220> FEATURE:
<223> OTHER INFORMATION: Synthetic Construct

<400> SEQUENCE: 23

Lys Ala Ser Gly Tyr Pro Phe Thr Arg Tyr Val Met His
         1               5                   10
```

<210> SEQ ID NO 24
<211> LENGTH: 14
<212> TYPE: PRT
<213> ORGANISM: Artificial Sequence
<220> FEATURE:
<223> OTHER INFORMATION: Synthetic Construct

<400> SEQUENCE: 24

Trp Val Arg Lys Ala Pro Gly Gln Gly Leu Glu Trp Met Gly
1               5                   10

<210> SEQ ID NO 25
<211> LENGTH: 17
<212> TYPE: PRT
<213> ORGANISM: Artificial Sequence
<220> FEATURE:
<223> OTHER INFORMATION: Synthetic Construct

<400> SEQUENCE: 25

Tyr Ile Asn Pro Tyr Asn Asp Gly Val Asn Tyr Asn Glu Glu Phe Lys
1               5                   10                  15

Gly

<210> SEQ ID NO 26
<211> LENGTH: 30
<212> TYPE: PRT
<213> ORGANISM: Artificial Sequence
<220> FEATURE:
<223> OTHER INFORMATION: Synthetic Construct

<400> SEQUENCE: 26

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys
                20                  25                  30

<210> SEQ ID NO 27
<211> LENGTH: 8
<212> TYPE: PRT
<213> ORGANISM: Artificial Sequence
<220> FEATURE:
<223> OTHER INFORMATION: Synthetic Construct

<400> SEQUENCE: 27

Ala Arg Asn Trp Asp Thr Gly Leu
1               5

<210> SEQ ID NO 28
<211> LENGTH: 11
<212> TYPE: PRT
<213> ORGANISM: Artificial Sequence
<220> FEATURE:
<223> OTHER INFORMATION: Synthetic Construct

<400> SEQUENCE: 28

Trp Gly Gln Gly Thr Thr Val Thr Val Ser Ser
1               5                   10

<210> SEQ ID NO 29
<211> LENGTH: 329
<212> TYPE: PRT
<213> ORGANISM: Artificial Sequence
<220> FEATURE:
<223> OTHER INFORMATION: Synthetic Construct

<400> SEQUENCE: 29

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val Ala Thr Gly Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Ser Thr Leu Pro Pro Ser Arg Glu Glu
225                 230                 235                 240

Met Thr Lys Asn Gln Val Ser Leu Met Cys Leu Val Tyr Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Val Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 30
<211> LENGTH: 98
<212> TYPE: PRT
<213> ORGANISM: Artificial Sequence
<220> FEATURE:
<223> OTHER INFORMATION: Synthetic Construct

<400> SEQUENCE: 30

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr

```
                    20                  25                  30

Phe Pro Glu Pro Val Thr Val Ser Trp Asn Ser Gly Ala Leu Thr Ser
                35                  40                  45

Gly Val Ala Thr Gly Pro Ala Val Leu Gln Ser Ser Gly Leu Tyr Ser
            50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 31
<211> LENGTH: 110
<212> TYPE: PRT
<213> ORGANISM: Artificial Sequence
<220> FEATURE:
<223> OTHER INFORMATION: Synthetic Construct

<400> SEQUENCE: 31

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
                100                 105                 110

<210> SEQ ID NO 32
<211> LENGTH: 106
<212> TYPE: PRT
<213> ORGANISM: Artificial Sequence
<220> FEATURE:
<223> OTHER INFORMATION: Synthetic Construct

<400> SEQUENCE: 32

Gly Gln Pro Arg Glu Pro Gln Val Ser Thr Leu Pro Pro Ser Arg Glu
1               5                   10                  15

Glu Met Thr Lys Asn Gln Val Ser Leu Met Cys Leu Val Tyr Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
        50                  55                  60

Phe Leu Tyr Ser Val Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
                100                 105
```

```
<210> SEQ ID NO 33
<211> LENGTH: 23
<212> TYPE: PRT
<213> ORGANISM: Artificial Sequence
<220> FEATURE:
<223> OTHER INFORMATION: Synthetic Construct

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 34
<211> LENGTH: 11
<212> TYPE: PRT
<213> ORGANISM: Artificial Sequence
<220> FEATURE:
<223> OTHER INFORMATION: Synthetic Construct

<400> SEQUENCE: 34

Arg Ala Ser Lys Asp Ile Ser Lys Tyr Leu Asn
1               5                   10

<210> SEQ ID NO 35
<211> LENGTH: 14
<212> TYPE: PRT
<213> ORGANISM: Artificial Sequence
<220> FEATURE:
<223> OTHER INFORMATION: Synthetic Construct

<400> SEQUENCE: 35

Trp Tyr Gln Arg Lys Pro Gly Asp Ala Pro Lys Leu Leu Ile
1               5                   10

<210> SEQ ID NO 36
<211> LENGTH: 8
<212> TYPE: PRT
<213> ORGANISM: Artificial Sequence
<220> FEATURE:
<223> OTHER INFORMATION: Synthetic Construct

<400> SEQUENCE: 36

Tyr Tyr Thr Ser Gly Tyr His Ser
1               5

<210> SEQ ID NO 37
<211> LENGTH: 32
<212> TYPE: PRT
<213> ORGANISM: Artificial Sequence
<220> FEATURE:
<223> OTHER INFORMATION: Synthetic Construct

<400> SEQUENCE: 37

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 38
<211> LENGTH: 9
<212> TYPE: PRT
<213> ORGANISM: Artificial Sequence
<220> FEATURE:
<223> OTHER INFORMATION: Synthetic Construct

<400> SEQUENCE: 38
```

```
Gln Gln Gly Asp Ala Leu Pro Pro Thr
1               5
```

<210> SEQ ID NO 39
<211> LENGTH: 10
<212> TYPE: PRT
<213> ORGANISM: Artificial Sequence
<220> FEATURE:
<223> OTHER INFORMATION: Synthetic Construct

<400> SEQUENCE: 39

```
Phe Gly Gly Gly Thr Lys Val Glu Ile Lys
1               5                   10
```

<210> SEQ ID NO 40
<211> LENGTH: 107
<212> TYPE: PRT
<213> ORGANISM: Artificial Sequence
<220> FEATURE:
<223> OTHER INFORMATION: Synthetic Construct

<400> SEQUENCE: 40

```
Arg Thr Val Ala Ala Pro Ser Val Phe Ile Phe Pro Pro Ser Lys Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 41
<211> LENGTH: 23
<212> TYPE: PRT
<213> ORGANISM: Artificial Sequence
<220> FEATURE:
<223> OTHER INFORMATION: Synthetic Construct

<400> SEQUENCE: 41

```
Arg Ile Gln Met Thr Gln Ser Pro Ser Ser Leu Ser Ala Ser Val Gly
1               5                   10                  15

Asp Arg Val Thr Ile Thr Cys
            20
```

<210> SEQ ID NO 42
<211> LENGTH: 11
<212> TYPE: PRT
<213> ORGANISM: Artificial Sequence
<220> FEATURE:
<223> OTHER INFORMATION: Synthetic Construct

<400> SEQUENCE: 42

```
Lys Ala Ser Asp His Ile Gly Lys Phe Leu Thr
1               5                   10
```

<210> SEQ ID NO 43

```
<211> LENGTH: 14
<212> TYPE: PRT
<213> ORGANISM: Artificial Sequence
<220> FEATURE:
<223> OTHER INFORMATION: Synthetic Construct

<400> SEQUENCE: 43

Trp Tyr Gln Asp Lys Pro Gly Lys Ala Pro Lys Leu Leu Ile
1               5                   10

<210> SEQ ID NO 44
<211> LENGTH: 8
<212> TYPE: PRT
<213> ORGANISM: Artificial Sequence
<220> FEATURE:
<223> OTHER INFORMATION: Synthetic Construct

<400> SEQUENCE: 44

Tyr Gly Ala Thr Ser Lys Leu Thr
1               5

<210> SEQ ID NO 45
<211> LENGTH: 32
<212> TYPE: PRT
<213> ORGANISM: Artificial Sequence
<220> FEATURE:
<223> OTHER INFORMATION: Synthetic Construct

<400> SEQUENCE: 45

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 46
<211> LENGTH: 9
<212> TYPE: PRT
<213> ORGANISM: Artificial Sequence
<220> FEATURE:
<223> OTHER INFORMATION: Synthetic Construct

<400> SEQUENCE: 46

Gln Gln Tyr Trp Ser Thr Pro Phe Thr
1               5

<210> SEQ ID NO 47
<211> LENGTH: 10
<212> TYPE: PRT
<213> ORGANISM: Artificial Sequence
<220> FEATURE:
<223> OTHER INFORMATION: Synthetic Construct

<400> SEQUENCE: 47

Phe Gly Gly Gly Thr Lys Val Glu Ile Lys
1               5                   10

<210> SEQ ID NO 48
<211> LENGTH: 105
<212> TYPE: PRT
<213> ORGANISM: Artificial Sequence
<220> FEATURE:
<223> OTHER INFORMATION: Synthetic Construct

<400> SEQUENCE: 48

Gly Gln Pro Lys Ala Ala Pro Ser Val Thr Leu Phe Pro Pro Ser Ser
1               5                   10                  15
```

```
Glu Glu Leu Gln Ala Asn Lys Ala Thr Leu Val Cys Tyr Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Trp Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys
            100                 105

<210> SEQ ID NO 49
<211> LENGTH: 15
<212> TYPE: PRT
<213> ORGANISM: Artificial Sequence
<220> FEATURE:
<223> OTHER INFORMATION: Synthetic Construct

<400> SEQUENCE: 49

Glu Pro Asp Ser Gly Asp Lys Thr His Thr Cys Pro Pro Cys Pro
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Synthetic Construct

<400> SEQUENCE: 50

Glu Pro Lys Ser Cys Asp Lys Thr His Thr Cys Pro Pro Cys Pro
1               5                   10                  15
```